US011690562B2

(12) United States Patent
Varghese et al.

(10) Patent No.: US 11,690,562 B2
(45) Date of Patent: Jul. 4, 2023

(54) SKIN GLOSS MEASUREMENT USING BREWSTER'S ANGLE

(71) Applicant: KONINKLIJKE PHILIPS N.V., Eindhoven (NL)

(72) Inventors: Babu Varghese, Eindhoven (NL); Arnoldus Johannes Martinus Jozeph Ras, Mierlo (NL); Rieko Verhagen, Vught (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 761 days.

(21) Appl. No.: 16/499,884

(22) PCT Filed: Apr. 2, 2018

(86) PCT No.: PCT/EP2018/058375
§ 371 (c)(1),
(2) Date: Oct. 1, 2019

(87) PCT Pub. No.: WO2018/185039
PCT Pub. Date: Oct. 11, 2018

(65) Prior Publication Data
US 2020/0113507 A1 Apr. 16, 2020

(30) Foreign Application Priority Data
Apr. 5, 2017 (EP) .................... 17165011

(51) Int. Cl.
*A61B 5/00* (2006.01)
*G01N 21/21* (2006.01)
*G01N 21/57* (2006.01)

(52) U.S. Cl.
CPC ............ *A61B 5/443* (2013.01); *A61B 5/0075* (2013.01); *A61B 5/0077* (2013.01); *G01N 21/21* (2013.01);
(Continued)

(58) Field of Classification Search
CPC ..... A61B 5/443; A61B 5/0075; A61B 5/0077; A61B 2562/0233; A61B 5/145; G01N 21/21; G01N 21/57
See application file for complete search history.

(56) References Cited

U.S. PATENT DOCUMENTS

| 7,289,211 B1 | 10/2007 | Walsh |
| 9,265,457 B2 | 2/2016 | Kudvelly |
| (Continued) | | |

FOREIGN PATENT DOCUMENTS

| JP | H07323013 | 12/1995 |
| JP | 2002112970 A | 4/2002 |
| (Continued) | | |

OTHER PUBLICATIONS

International Search Report and the Written Opinion dated Aug. 8, 2018, for International Application No. PCT/EP2018/058375.
(Continued)

*Primary Examiner* — Jason M Sims
*Assistant Examiner* — Abid A Mustansir

(57) ABSTRACT

A system includes a sensor for measuring a skin parameter. The sensor includes at least three spatially separated light sources for providing unpolarized visible light, a detector located at a first distance from each of the light sources selected from the range of 10-80 mm and at a second distance from the skin, and a polarizer including one or more of a segmented polarizer and a spatially varying polarizer. In a sensing mode, the light sources are configured to sequentially illuminate the skin with the light with optical axes at an angle of incidence selected from the range of 10°-80°, and the detector is configured to sequentially detect light reflected from the skin and generate corresponding detector signals.

17 Claims, 10 Drawing Sheets

(52) U.S. Cl.
CPC ...... *G01N 21/57* (2013.01); *A61B 2562/0233* (2013.01)

(56) References Cited

U.S. PATENT DOCUMENTS

| | | | |
|---|---|---|---|
| 9,452,113 | B2 | 9/2016 | Kanoun-Copy |
| 10,976,239 | B1* | 4/2021 | Hart ................ G02B 27/646 |
| 2003/0045799 | A1* | 3/2003 | Bazin .................. G01N 21/84 |
| | | | 600/476 |
| 2003/0086703 | A1 | 5/2003 | Kollias |
| 2003/0138249 | A1 | 7/2003 | Merola |
| 2004/0257439 | A1 | 12/2004 | Shirai |
| 2010/0185064 | A1 | 7/2010 | Bandic |
| 2010/0249731 | A1 | 9/2010 | Stamatas |
| 2011/0013006 | A1 | 1/2011 | Uzenbajakava |
| 2013/0085351 | A1* | 4/2013 | Kudavelly ......... A61B 5/14558 |
| | | | 600/315 |
| 2013/0148326 | A1 | 6/2013 | Goldfain |
| 2014/0055661 | A1 | 2/2014 | Imamura |
| 2014/0155754 | A1* | 6/2014 | Varghese ................ B26B 19/48 |
| | | | 606/9 |
| 2015/0062380 | A1 | 3/2015 | Nakamura |
| 2015/0127071 | A1 | 5/2015 | Kanoun-Copy |
| 2015/0223749 | A1* | 8/2015 | Park .................. G01N 21/6486 |
| | | | 600/476 |
| 2017/0135625 | A1 | 5/2017 | Varghese |
| 2018/0168456 | A1 | 6/2018 | Lim |
| 2018/0184967 | A1* | 7/2018 | Yoshida ................ A61B 5/442 |

FOREIGN PATENT DOCUMENTS

| | | |
|---|---|---|
| JP | 2009297295 A | 12/2009 |
| JP | 2015039570 A | 3/2015 |
| JP | 2016126134 A | 7/2016 |
| JP | 2017027618 A | 2/2017 |
| WO | 2018185142 | 10/2018 |
| WO | 2018185212 | 10/2018 |

OTHER PUBLICATIONS

S. Junger et al. "Polarization-and wavelength-sensitive sub-wavelength structures fabricated in the metal layers of deep submicron CMOS processes" SPIE Photonics Europe. International Society for Optics and Photonics (2010).

Jürgen Ernst et al., "Nanostructured Optical Filters in CMOS for Multispectral, Polarization and Image Sensors," Microelectronic Systems (2011).

Jenkins and White, "Fundamentals of Optics," McGraw-Hill Book Company, Inc., 1957, Chapter 25 Reflection, 523-526 and Figure 25B.

* cited by examiner

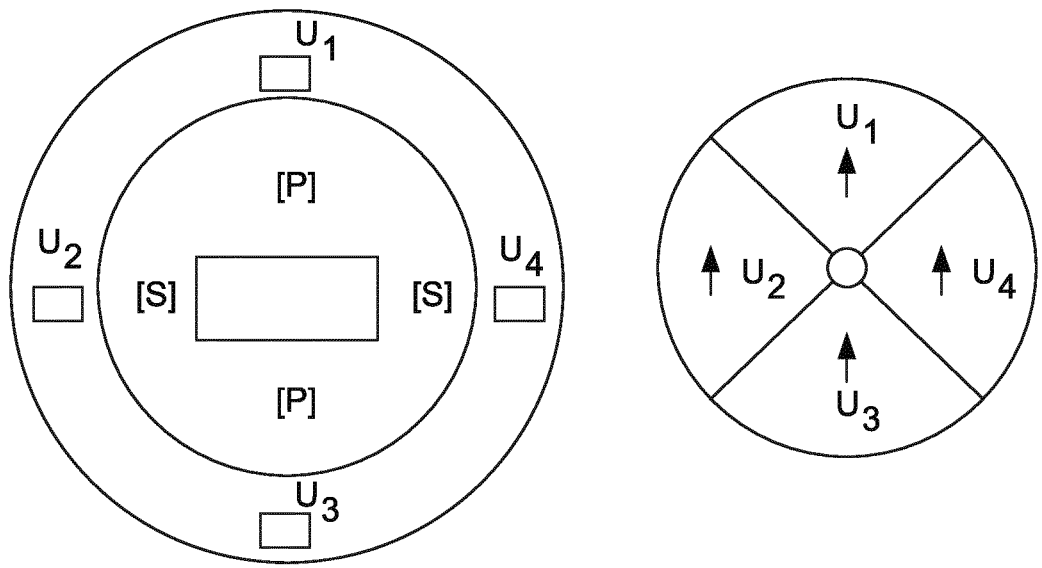
FIG. 5A
FIG. 5B
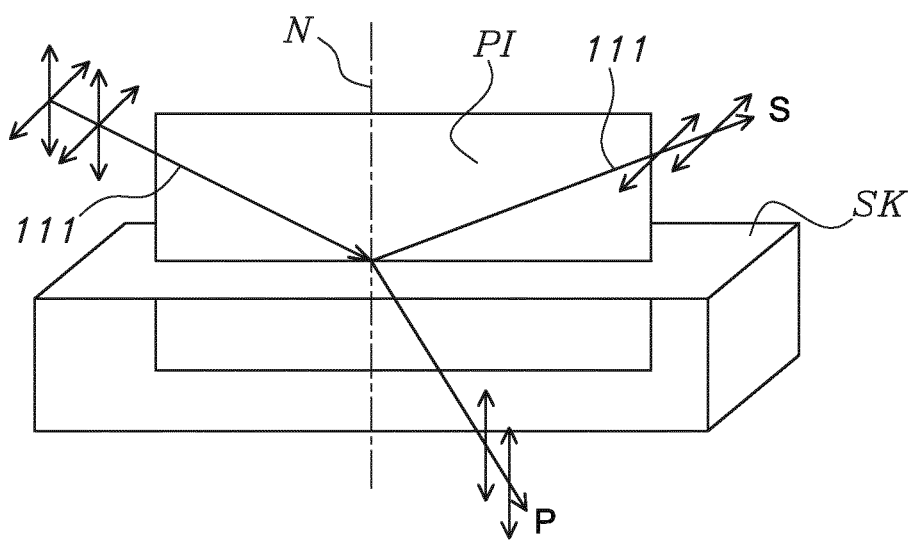
FIG. 6

SKIN GLOSS MEASUREMENT USING BREWSTER'S ANGLE

CROSS REFERENCE TO RELATED APPLICATIONS

This application is the U.S. National Phase application under 35 U.S.C. § 371 of International Application No. PCT/EP2018/058375 filed Apr. 2, 2018, published as WO 2018/185039 on Oct. 11, 2018, which claims the benefit of European Patent Application Number 17165011.2 filed Apr. 5, 2017. These applications are hereby incorporated by reference herein.

FIELD OF THE INVENTION

The invention relates to a system comprising a sensor for measuring skin gloss. The invention further relates to a method for evaluation skin gloss.

BACKGROUND OF THE INVENTION

Skin gloss relates issues are known in the art. US2015127071 (see also equivalents U.S. Pat. No. 9,452,113B2 or WO2013186716A2) is related to a treatment of oily skin and describes that the skin is rich in sebaceous glands and is continually renewed. US2015127071 further describes that the secretion of sebum is a normal phenomenon which is useful to both the skin and the head of hair. Sebum is normally an agent for moisturizing the epidermis. It is the natural product of the sebaceous gland, which is an annex of the pilosebaceous unit. It is essentially a more or less complex mixture of lipids. Sebum protects the skin and also the scalp and gives the hair sheen by lubricating the cuticle.

According to US2015127071, a hypersecretion of sebum, or seborrhoea, may lead to aesthetic disorders. Thus, an excessive secretion of sebum may result in oily skin with a shiny or glistening appearance and it may also promote the appearance of an oily dandruff condition of the scalp or oily dandruff. It may be accompanied by an increase in pore size. For example, stress, fatigue and the winter period may be factors that intensify these conditions in the majority of people. Among the population having oily skin, it is possible to find subjects who have endocrine disorders or neurological disorders, or obese subjects. It is also possible to find adolescents, people suffering from excess hormones (in particular male hormones), menstruating women or menopausal women who have oily skin.

US2003045799 describes a portable device for observing a typological characteristic of the body. For example, the device can be used to observe at least one characteristic of the appearance of the skin or the hair. The device can generate at least two images of the zone under examination. The images differ from each other as to a feature other than magnification and the intensity of the light source.

US2010249731 describes a method for measuring skin erythema comprising: a) acquiring a digital image of skin under orthogonal polarization conditions with a white calibration standard included in the field of view of the image; b) identifying median intensity values for a red, a green, and a blue channel for the white standard; c) calculating skin reflectance values given by the red, green, and blue intensity values of each pixel of the image to absorbance values by taking the logarithm of the ratio of the white standard values divided by the skin reflectance values at each of the red green and blue channels separately, where the absorbance equals: log(Iwhite(red,green,blue)/Iskin(red,green,blue)) for all pixels representing skin; d) subtracting the red channel absorbance values from the green channel absorbance values for all pixels representing skin; e) subtracting the red channel absorbance values from the blue channel absorbance values for all pixels representing skin; f) calculating the ratio of the value calculated at step (d) divided by the value calculated at step (e); and g) building an intensity map of the ratio calculated at step (f).

US2014055661 describes an imaging apparatus including a lens optical system, an imaging device including a plurality of first and second pixels, and an arrayed optical device, wherein the lens optical system includes a first optical region which primarily passes therethrough light oscillating in a direction of a first polarization axis and a second optical region which passes therethrough light oscillating in every direction; and the arrayed optical device makes light having passed through the first optical region incident on the first pixels and makes light having passed through the second optical region incident on the second pixels.

JPH07323013 describes a method for observing the surface of a skin by dividing the reflected light reflected on the surface of the skin into two light paths and receiving simultaneously the reflected lights with different polarized components from the first filter for light receiving and the second filter for light receiving. The first polarized light filter for light receiving is fitted in a light path for a light transmitted through a half mirror among reflected light from a skin and furthermore, in a light path for the light reflected on a mirror, the second polarized light filter for light receiving with the polarized light direction being different from that for the first polarized light filter for light receiving, is set. Then, a specified polarized light is emitted on the skin through a polarized light filter from a ring illuminating apparatus and the reflected light is received by the first CCD camera through the first polarized light filter for light receiving. In addition, the reflected light from the skin is received by the second CCD camera through the second polarized light filter for light receiving and these image signals are inputted into the same image processing part.

SUMMARY OF THE INVENTION

The appearance of skin is significantly influenced by the presence of a thin emulsified film on the skin surface. Sebum containing lipids from sebaceous glands and epidermal keratinocytes is mixed with sweat and other lipids from cosmetics and environment to form this emulsified film of refractive index higher than that of epidermis. Sebum causes the skin to look glossier due to higher Fresnel reflection and smooth air-sebum interface. Optimal balance between sebum production and requirements imparts a non-glossy and healthy feel to the skin and is dermatologically and cosmetically desirable. Glossy and oily skin is considered to be unaesthetic and unpleasant and often associated with various dermatological disorders such as seborrhea, acne and hormonal imbalance. In sebum deficit conditions, the skin is vulnerable to infections and it feels itchy, dry, and looks lusterless, erythematous, and scaly.

As a result strategies to balance the needs of the skin to its optimal lipid requirements by controlling the sebum secretion rate and/or to monitor the skin condition using non-invasive optical devices and methods seem necessary.

Devices for measuring skin glossiness are known in the art. However, they may e.g. suffer from a dependency of the rotational position on the skin and/or may not be able to provide quantitative results. Hence, it is an aspect of the invention to provide an alternative device (herein further the more general term "system" is applied) and/or skin gloss sensing method, which preferably further at least partly obviate(s) one or more of above-described drawbacks. The present invention may have as object to overcome or ameliorate at least one of the disadvantages of the prior art, or to provide a useful alternative.

Amongst others, the invention provides a system ("system" or "skin sensor system") comprising a sensor for measuring a skin parameter, such as especially selected from one or more of the group consisting of skin gloss and skin oiliness ("sensor" or "skin gloss sensor"), the sensor comprising (i) a plurality of spatially separated light sources configured to provide light source light ("light"), and (ii) a detector configured at a first distance (d1) from each of the light sources, wherein the sensor is configured to provide the light source light with optical axes (OL) under an angle of incidence ($\alpha$), especially selected from the range of 10-80°, with the skin at a second distance (d2) and to detect reflected light source light (reflected at the skin), wherein the sensor comprises at least two light sources, even more especially at least three light sources, wherein the light sources are especially configured to provide unpolarized visible light source light, even more especially white light, wherein the first distance (d1) may especially be selected from the range of 1-100 mm, like 5-80 mm, especially 5-60 mm, more especially 5-50 mm, such as especially 5-30 mm, and wherein the detector is configured to detect polarized light.

With such system, it is possible to sense skin gloss in a relatively reliable way, with a reduced influence of rotation of the sensor relative to the skin. Further, with such system it may be possible to quantitatively estimate skin gloss. The term "skin gloss" herein refers to gloss of the skin but may also refer to "skin oiliness". Hence, the term "skin gloss" herein may also be defined as "skin parameter especially selected from one or more of the group consisting of skin gloss and skin oiliness". The values that may be measured with the system as described herein may reflect skin gloss and skin oiliness, as skin gloss may be related to skin oiliness. Herein, the term "skin gloss" is sometimes used to indicate both skin gloss or skin oiliness. Hence, in embodiments the term skin gloss may refer to skin gloss or skin oiliness, or especially to skin gloss.

As indicated above, the invention provides a system comprising a sensor. The term "system" may refer to a single device, e.g. having its own housing, but may also refer to a plurality of functionally coupled devices, such as e.g. the sensor and a control system or a control system comprising device, such as a computer, a smartphone etc. In embodiments, the term "sensor" may also refer to a plurality of sensors.

Especially, the system comprises a housing, such as the system comprising a device comprising a housing. The sensor may essentially be contained by the housing. The housing may include an aperture. Such aperture may provide a field of view to the detector. Further, the housing with aperture may also provide the second distance, which may be defined as the distance between the aperture (i.e. the skin when the sensor is configured on the skin) and the detector (or the last optics, especially a lens, before the detector (when seen from the detector)). The second distance may also be indicated as the free working distance, and may be defined as the distance between the aperture and the detector, or, when optics are available, between the aperture and the last optics (seen from the detector in the direction of the aperture). Hence, the second distance may also be indicated as the distance during operation between the skin and the detector, or, when optics are available, between the skin and the last optics (seen from the detector in the direction of the aperture). The housing can be seen as a distance holder, as it defines a distance between the skin and the detector (or its last optics). Such optics are configured upstream of the detector; i.e. the detector is configured downstream of such (optional) optics. The second distance may be in the order of 10-45 mm, but may even be up to 200 mm. Hence, in embodiments the second distance may be selected from the range of 10-200 mm, such as 10-30 mm, or in the range of 40-80 mm. The detector is configured to detect the reflected light. Hence, the detector detects the reflected light for imaging during (sequential) illumination by the (unpolarized) light sources. The detector essentially only detects polarized light, e.g. due to a polarizer upstream of the detector. An optical axis of the detector and an optical axis of the sensor may essentially coincide. Further, the optical axis of the sensor and a net optical axis of all light sources may essentially coincide.

The light sources are especially configured such that they are at a first distance from the detector, which first distance is smaller than the (relevant) field of view (dimensions). Further, the plurality of light sources may especially include sets of two (or more) light sources that are configured equidistant to the detector. Such sets may be controlled independently. Further, the first distances are not necessarily equal for each of the light sources. Hence, the phrase "the detector configured at a first distance (d1) from each of the light sources" and similar phrases may also be interpreted as "the light sources configured at first distances (d1) from the light sources, wherein the first distances for each of the light sources may be identical, or wherein there are two or more different first distances". As indicated herein, the first distance may especially be selected from the range of 1-100 mm.

Hence, the invention provides (in an aspect (also)) a system comprising a sensor for measuring a skin parameter, the sensor comprising (i) a plurality of spatially separated light sources configured to provide light source light, and (ii) a detector configured at a first distance from each of the light sources, wherein the sensor is configured to provide the light source light with optical axes under an angle of incidence ($\alpha$) selected from the range of 10-80°, wherein during operation the sensor is (to be) configured on the skin, with an aperture of a housing of the sensor on the skin, and to detect reflected light source light (which is reflected at the skin), wherein the sensor comprises at least three light sources, wherein the light sources are configured to provide visible light source light, wherein the visible light source light is unpolarized, and wherein the first distance is selected from the range of 10-80 mm, wherein the detector is configured to detect polarized light. The system may include further features as defined in the accompanying embodiments.

The system may include a memory, a processing device (or "processor" or "processor system" or "controller" or "control system"), a user interface, and an indication unit for indicating a sensed skin gloss value, such as a LED indicator (e.g. suitable for indicating different values by switching on 0-n LEDs in dependence of the sensed value, wherein n is the number of LEDs used for indicating a maximum sensed value, with n in general being equal to or larger than two, such as at least three) and/or a display.

Examples of user interface devices include a manually actuated button, a display, a touch screen, a keypad, a voice activated input device, an audio output, an indicator (e.g., lights), a switch, a knob, a modem, and a networking card, among others. Especially, the user interface device may be configured to allow a user instruct the device or apparatus with which the user interface is functionally coupled by with the user interface is functionally comprised. The user interface may especially include a manually actuated button, a touch screen, a keypad, a voice activated input device, a switch, a knob, etc., and/or optionally a modem, and a networking card, etc. The user interface may comprise a graphical user interface. The term "user interface" may also refer to a remote user interface, such as a remote control. A remote control may be a separate dedicate device. However, a remote control may also be a device with an App configured to (at least) control the system or device or apparatus.

The controller/processor and the memory may be any type. The processor may be capable of performing the various described operations and executing instructions stored in the memory. The processor may be an application-specific or general-use integrated circuit(s). Further, the processor may be a dedicated processor for performing in accordance with the present system or may be a general-purpose processor wherein only one of many functions operates for performing in accordance with the present system. The processor may operate utilizing a program portion, multiple program segments, or may be a hardware device utilizing a dedicated or multi-purpose integrated circuit.

The sensor comprises (i) a plurality of spatially separated light sources configured to provide light source light ("light"). Especially, the sensor comprises at least three spatially separated light sources.

The term "light source" may comprise a semiconductor light-emitting device, such as a light emitting diode (LEDs), a resonant cavity light emitting diode (RCLED), a vertical cavity laser diode (VCSELs), an edge emitting laser, etc. The term "light source" may also refer to an organic light-emitting diode, such as a passive-matrix (PMOLED) or an active-matrix (AMOLED). In a specific embodiment, the light source comprises a solid state light source (such as a LED or laser diode). In an embodiment, the light source comprises a LED (light emitting diode). The term LED may also refer to a plurality of LEDs. Further, the term "light source" may in embodiments also refer to a so-called chips-on-board (COB) light source. The term "COB" especially refers to LED chips in the form of a semiconductor chip that is neither encased nor connected but directly mounted onto a substrate, such as a PCB. Hence, a plurality of semiconductor light sources may be configured on the same substrate. In embodiments, a COB is a multi LED chip configured together as a single lighting module.

Further, the light sources are configured to provide unpolarized light source light. This allows the sensor derive information from the polarization direction of the reflected light.

Further, the light sources are especially configured to provide white light. The term white light herein, is known to the person skilled in the art. It may especially relate to light having a correlated color temperature (CCT) between about 2000 and 20000 K, especially 2700-20000 K, for general lighting especially in the range of about 2700 K and 6500 K, and for backlighting purposes especially in the range of about 7000 K and 20000 K, and especially within about 15 SDCM (standard deviation of color matching) from the BBL (black body locus), especially within about 10 SDCM from the BBL, even more especially within about 5 SDCM from the BBL. Especially, the white light may be provided by a blue LED with a yellow emitting luminescent material. Such light source can provide white light that is essentially not polarized.

The sensor comprises a plurality of spatially separated light sources. This implies that there is some distance between the light sources. Especially, the light sources are configured with the detector in between. Further, especially the maximum number of light sources is about twelve, such as ten, like eight, such as six or four or three. Up to about twelve, even more especially up to about eight, such as up to about six allows a configuration around the sensor which also allows a spatial separation between adjacent light sources which may (also) be in the order of about 1-100 mm, such as at least 5 mm, like at least 10 mm.

Hence, in embodiments the system comprises at least three light sources. In yet further embodiments, the sensor has a sensor optical axis, and the light sources are configured rotationally symmetric around the sensor optical axis. In embodiments, the light sources may be configured relative to each other under angles with the optical axis of 360°/n, wherein n is the number of light sources. Hence, in embodiments wherein the system comprises at least three or four light sources, the mutual angles with the optical axis may be 120° and 90°, respectively.

Therefore, as indicated above, the system comprise especially at least two light sources, even more especially at least three light sources, and the light sources are especially configured to provide unpolarized visible light source light, even more especially white light.

In embodiments, the system may especially comprise a plurality of light sources providing visible light source light, wherein the visible light source light is unpolarized, especially wherein essentially all visible light source light is unpolarized. Especially, each of the light sources provides essentially unpolarized visible light source light. Hence, these embodiments provide the skin with unpolarized light source light, wherein the light source light is essentially not partially polarized. Therefore, especially the light sources are configured to provide visible light source light, wherein the visible light source light is unpolarized.

As further indicated above, the system also comprises a detector configured at a first distance (d1) from each of the light sources. Good results were obtained with the first distance (d1) being in the range of about 1-80 mm. Hence, in specific embodiment the first distance may by be selected from the range of 1-80 mm, especially from the range of 2-60 mm, such as in the range of 5-20 mm, like in the range of 6-14 mm.

Especially, the detector is configured to detect polarized light. To this end, the detector may comprises a polarizer, which is configured upstream of the detector. In this way, only polarized light, especially S-polarized light, may be received by the detector. Below, some specific embodiments of the polarizer are further elucidated.

Especially, the detector is configured to detect polarized light. Hence, the sensor may comprise a polarizer configured upstream of the detector. The polarizer may filter the reflected light source light (reflected at the skin) such that the detector receives polarized light, especially S-polarized light, or alternatively especially P-polarized light.

In specific embodiments, the sensor is configured to provide the light source light with optical axes (OL) under an angle of incidence ($\alpha$), especially selected from the range of 10-80°, with the skin at a second distance (d2) and to detect reflected light source light (reflected at the skin). Of course, the skin is not part of the system. However, the system is especially configured to measure skin at a second distance. For instance, the system may include a distance holder or other element, which allows configuration of the sensor at the second distance. At this distance, the above indicated angle of incidence may be achieved, which is in the range of 10-80°, more especially 20-80°. In specific embodiments, which are further elucidated below, the angle is selected from the range of 20-60°.

The distance holder is configured to be placed on the skin such that the skin is at a second distance to the detector or the last optics before the detector (seen from the detector). Especially, the distance holder may be configured to be placed flat on the skin such that the skin is at a second distance to the detector or last optics before the detector (seen from the detector). The distance holder may be comprised in a housing of the sensor. Especially, the system may comprise a housing at least partially enveloping the sensor, wherein the housing comprises the distance holder. Alternatively, the system may comprise a housing and a (separate) distance holder; in such embodiments the second distance may further be increased. Also a distance holder other than a housing may comprise an aperture.

The system, or at least part thereof, such as the housing, may be configured to be pressed on the skin. Hence, 'on the skin' may indicate that the system, or at least part thereof, is pressed against the skin (during use), especially wherein the distance holder, such as a housing, is pressed against the skin. Hence, the term "second distance" especially refers to the distance between the detector, or its last optics (seen from the detector), and the skin, during use of the system. The second distance is a non-zero distance between the aperture/skin and the detector (or optics upstream of the detector, when such optics are available). The term optics may especially refer here to a lens.

In specific embodiments, the detector comprises a 2D camera, such as a CCD camera TD-Next 5620 M7_1A and TD-Next 5640 M12_3B. Each pixel may essentially consist of three pixels for blue, green, and red, respectively. This may provide the detector blue, green, and red channels intensity separately.

In embodiments, the detector may have a detector area of about 10*10 mm². The detector may have in the order of 1 Megapixel or more.

In further embodiments, the sensor may further comprise a focusing lens configured upstream of the detector. The focusing lens may be configured to have at one side the detector in focus and/or at the other side of the lens the skin in focus. The lens may allow a good image of the skin at the detector.

In embodiments, the sensor may further comprise an aperture configured upstream of the detector and upstream of the focusing lens. This may further add to resolution. The aperture may in embodiments have a diameter selected from the range of 0.1-5 mm, more especially 0.1-2 mm, like especially 0.1-0.8 mm.

The optical axis of the system may be configured perpendicular to the detector.

In specific embodiments, the system may further comprise an analysis system. The analysis system is configured to generate a corresponding skin sensor value in dependence of a sensor signal of the sensor. The analysis system and sensor may be incorporated in a single device, such as skin cleansing device, skin rejuvenation device, etc. Hence, in embodiments the system comprises a skin care device, like such skin cleansing device, skin rejuvenation device, etc., wherein the skin care device comprises the sensor and the analysis system. The analysis system can translate the signal of the sensor, more especially of the detector, into a signal that may contain useful information of the user, such as an indication of the skin glossiness on an indicator unit (such as a display or LED bar). The skin sensor value can be the skin parameter of may be further processed into the skin parameter based on predefined relations between the skin sensor value and the skin parameter.

In other embodiments, however, the sensor may be comprised by a separate device, that is wired or wireless coupled to an analysis system. For instance, such analysis system may be comprised by a smartphone. For instance, an App may be used to readout the sensor and display a skin sensor value based on the sensor signal generated by the sensor. Therefore, in yet other embodiments the system comprises (i) a skin care device, wherein the skin care device comprises the sensor, and (ii) a second device functionally coupled to the skin care device, wherein the second device comprises the analysis system. The term "analysis system" may also refer to a plurality of interrelated systems. For instance, the sensor may (further) comprise a processor and an external device may comprise a processor which may communicate with each other. The processor of the sensor may provide the sensor signal, and the processor of the external device generates on the basis thereon the skin sensor value, indicative of the glossiness/oiliness of the skin.

The sensor signal may be the detector signal. In other embodiments, the sensor signal may be a processed detector signal. Hence, the phrase "base on the detector signal" may in embodiments also refer to a processed detector signal. Based on the sensor signal, i.e. essentially based on the detector signal, the analysis system may provide a corresponding skin sensor value.

When the system comprises a functional device, such as a skin cleansing device or skin rejuvenation device, the device may be configured to execute an action in dependence of the sensor signal of the sensor (for sensing gloss) (or skin sensor value). For instance, when a certain lower or upper threshold of skin gloss (or skin oiliness) is reached, the functional device may provide a signal to the user, like a sound or vibration signal. Alternatively or additionally, the functional device may reduce or increase specific actions in dependence of the sensor signal, such as in increased or reduced massaging of the skin in dependence of the sensor signal.

Therefore, in yet a further aspect the invention also provides a method of sensing skin gloss, the method comprises providing light source light with the system as defined herein to a skin and sensing with the system the reflected light source light reflected at the skin.

The method is especially executed with the sensor on the skin, such as with a housing comprising an aperture on the skin, whereby during operation there is a second distance between the skin and the detector, or its last optics.

Especially, the method is a non-medical method. Especially, the method is a cosmetical method.

Also, in yet a further aspect the invention provides a data carrier having stored thereon program instructions, which when executed by the system as defined herein causes the system to execute the method as defined herein.

As indicated above, the system may comprise a polarizer. The polarizer is configured to allow only one or more specific polarizations enter the detector. Hence, in specific embodiments the sensor comprises a polarizer configured upstream of the detector. Even more especially, the polarizer comprises one or more of (i) a segmented polarizer and (ii) a spatially varying polarizer. This allows a reduction of the influence of the (rotational) position of the detector, especially when the light sources are driven sequentially. In this way, the sensor may detect the reflected light as function of the light source. With the different polarizations of the polarizer, the sensitivity of the system may be higher.

Therefore, in specific embodiments, the device comprises a sensing mode, wherein the light sources are configured to sequentially provide the light source light. In further specific embodiments, the detector may be configured to sequentially detect reflected light source light sequentially generated by the light sources, and configured to generate corresponding detector signals. As indicated above, the system further comprises an analysis system, with the analysis system being configured to generate a corresponding skin sensor value in dependence of a sensor signal of the sensor, and in specific embodiments wherein the skin sensor value is based on an average of respective detector signals.

In embodiments, the segmented polarizer comprises a pixelated wire grid polarizer with two or more pixels having different polarization orientations. Here, the term "pixels" may also refer to areas. Especially, the sensor comprises n light sources, such as four light sources, and wherein the segmented polarizer comprises a pixelated wire grid polarizer with n pixels having polarization orientations perpendicular to each other, such as two sets of two pixels (in the case of four light sources). As indicated above, the value of n is especially at least 2, such as 3 or 4, or more.

In embodiments, the spatially varying polarizer comprises one or more of an azimuthal varying polarizer and a radial varying polarizer, which especially allows more number of emitters to be configured very close to each other.

Best results may be obtained at about the Brewster angle. Hence, in embodiments the sensor is configured to provide the light source light with optical axes (OL) under an angle of incidence ($\alpha$) with the skin at a second distance (d2), wherein the angle of incidence ($\alpha$) is selected from the range of 50-60°, even more especially wherein the angle of incidence ($\alpha$) is selected from the range of 52-56°.

Hence, amongst others herein skin gloss measurement systems and methods using sequential illumination from multiple unpolarized light emitters illuminating the skin at an angle of incidence (essentially) equal to Brewster's or polarization angle and a segmented or spatially varying polarizer in the detection path are provided.

Especially good results may (thus) be obtained when the light sources are sequentially driven. As the light sources are configured at different positions, the reflection behavior and polarization behavior, as well as an angular dependency of the reflected light may in this way provide additional information (that may result from skin structure and/or, non-uniformity of illumination) and/or may allow reducing the dependence of the sensor on the rotational position on the skin.

Hence, in specific embodiments the device comprises a sensing mode, wherein the light sources are configured to sequentially provide the light source light.

For instance, the sensors may have a measuring frequency in the range of 0.1*n-100*n Hz, wherein n is the number of light sources. With for instance 1*n Hz, each second all light sources have been consecutively illuminated the skin and the detector has (consecutively) measured possible reflections based on the respective light sources.

Of course, the use of a plurality of light sources may also allow addressing of subsets of two or more light sources. For instance, it may also be possible when four light sources are used to have two sets of two light sources, which are configured opposite of each other (with the detector in between) which sets of light sources are alternatingly switched on and off.

Also combinations of such methods may be applied, wherein e.g. in time the composition of the set of light sources may change. For instance, in a mode during a predetermined time the light sources are addressed sequentially and in a subsequent predetermined time the light sources are addressed as a group. Such mode may include a repetition of these respective predetermined times. All kind of illumination schemes may be used to further create a more reliable measuring of the skin gloss.

The detector signal may be an average over the signals generated by the respective light sources. Hence, in yet further embodiments the detector is configured to sequentially detect reflected light source light sequentially generated by the light sources, and configured to generate corresponding detector signals, wherein the system further comprises an analysis system, wherein the analysis system is configured to generate a corresponding skin sensor value in dependence of a sensor signal of the sensor, and wherein the skin sensor value is based on an average of respective detector signals. Hence, especially the detector signals are first processed and then averaged. In this way the detector signal may be an average over the signals generated by the respective light sources.

As indicated above, the system may comprise at least three light sources. Yet further, as indicated above in embodiments the sensor has a sensor optical axis (O2), and wherein the light sources are configured rotationally symmetric around the sensor optical axis (O2).

In further specific embodiments, as also indicated above, the system may further comprise an analysis system wherein the analysis system is configured to generate a corresponding skin sensor value in dependence of a sensor signal of the sensor. There may be a number of ways in which the sensor signal is generated. Even though many low cost devices are reported for home-use applications, the gloss measurements using these devices appear not to be quantitative and also may not correlate with the subjective perception and reference device measurements. Methods for estimating the gloss may be based on counting the number of white pixels above a certain threshold in the camera images obtained using unpolarized illumination. However, it appears that the gloss estimation based on the number of white pixels depends on the incident light intensity levels (and its fluctuations), threshold and variation in the optical properties of skin (inter and intra-individual variations), which is less desirable.

Here below, some specific embodiments are described which may provide more reliable results.

Hence, in embodiments especially the system is configured to create an image of the skin with the detector, wherein the image of the skin comprises a first area wherein maximum intensity is sensed and a second area at a first image distance from the first area, wherein the first area and second area do not overlap, wherein the system is further configured to generate the skin sensor value based on an intensity dependent of the reflected light source light along a path between the first area and the second area. The image may have an image area. The first and the second area may be areas of e.g. 0.05-30%, such as 0.05-15%, like 0.1-10% of the image area. Further, first image distance, i.e. the distance between the first area and second area, more precisely the shortest distance between the boundaries of these two areas, may be in the order of at least the area size of the first area or the second area. In general, the first area and second area may be essentially the same. Optionally, the areas may also be different but then a correction factor may be applied. Further, in general these areas are chosen square or rectangular, especially square. The area wherein a maximum intensity is sensed may be the area of the image where essentially specular reflection takes place, i.e. where the light source light is mirror like reflected and detected by the detector.

Hence, the first image distance may be in the range the square root of 0.05-30% of the image area, such as the square root of 0.05-15% of the image area, like the square root of 0.1-10% of the image area. Especially, the distance between the first area and the second area is at least 5% of the square root of the image area. Note that the image area may not have a fixed value, but may e.g. depend upon the magnification.

Further, note that the term "creating an image" and similar terms may not necessarily include the creation of a real image at a moment in time but may also refer to reading out the values of the detector at different positions over the detector surface.

It appears that information that can be derived from the two areas and/or from a (straight) line or the area in between those two areas can provide information over the glossiness, which may allow quantifying of the skin gloss (including skin oiliness), especially when the system has been calibrated (see also below).

Therefore, in embodiments the system may be configured to generate the skin sensor value based on a slope of a curve defined by the intensity of the reflected light source light along the path between the first area and the second area. Hence, based on the slope of the curve or an angle of the curve, it appears that useful skin gloss values can be generated.

Alternatively or additionally, the system may be configured to generate the skin sensor value based on an area below a curve defined by the intensity of the reflected light source light along the path between the first area and the second area. Hence, also based on the area under the curve or an angle of the curve, it appears that useful skin gloss values can be generated. The path can also be indicated as a straight trajectory or line.

Yet alternatively or additionally, the system may be configured to generate the skin sensor value based on a number of pixels of the image above a predefined threshold. Hence, based on the number of pixels above threshold also it appears that useful skin gloss values can be generated.

Further, alternatively or additionally, the system may be configured to generate the skin sensor value based on an average number of pixels of the image above predefined thresholds weighted with the corresponding pixel intensity, respectively. Therefore, also based on the weighted number of pixels above threshold useful skin gloss values can be generated.

Yet, alternatively or additionally the system may be configured to generate the skin sensor value based on a relation between an integrated intensity of the first area and the second area. Therefore, also the ratio specular to diffuse intensity of these respective ratios may be used for generating skin gloss values. For instance, when the system is calibrated with an essentially specularly reflective area and with an essentially diffuse reflective area, skin gloss parameters can be derived from the ratio specular to diffuse intensity of these respective ratios.

Further, alternatively or additionally, system is configured to define binary large objects ("blob") in the image, and wherein the system is configured generate the skin sensor value based on or more of average size and maximum size of the binary large objects in the image. Hence, based on the number of blobs and/or sizes of the blobs also useful skin gloss values can be generated. Hence, in this embodiment not the number of white pixels is used per se, but blobs are defined. Hence, also a threshold may be defined for those blobs, like at least k number of adjacent pixels over a specific intensity threshold value.

In above-mentioned embodiments, a number of times calibration has been mentioned. Especially for a quantitative evaluation of the skin gloss or skin oiliness, a calibration of the system, more precisely of the sensor (and in fact thus the detector) may be useful. This calibration can be done after production of the sensor. Alternatively or additionally, the calibration may software implemented for each sensor based on one or more earlier calibrations of example sensors. Calibration may also be part of a measuring process or may be regularly scheduled. In a specific embodiment, calibration is applied once after production of the sensor. Further, the system may include control routines that may update the calibration on the basis of sensor parameters of a reference sensor or based on e.g. drift in the signal, etc. etc.

In specific embodiments, the system is configured to generate a corresponding skin sensor value in dependence of a sensor signal of the sensor after a flat-field correction. Flat-field correction is a technique used to improve quality in digital imaging. Flat-field correction is especially used to compensate for the artifacts from 2-D images that are caused by non-uniformity of illumination and detection, variations in the pixel-to-pixel sensitivity of the detector and/or by distortions in the optical path. As indicated above, the flat-field correction may be based on a measurement with purely diffuse reference, such as e.g. diffuse standard like Spectralon. Based on such measurements, a flat-field correction may be provided, which may be used in any measurement (as herein described).

In yet further embodiments, the system is configured to generate a corresponding skin sensor value in dependence of a sensor signal of the sensor based on an average of the respective signals of red, green, and blue channels of the detector.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIGS. 5a-5b show schematic representations of the detected polarization states when multiple emitters are used for illumination in a ring configuration and polarizer with uniform polarization properties are used in the detection path;

FIG. 6: Reflection and transmission of unpolarized light at an interface;

The schematic drawings are not necessarily to scale.

DETAILED DESCRIPTION OF THE EMBODIMENTS

Figure 1A:
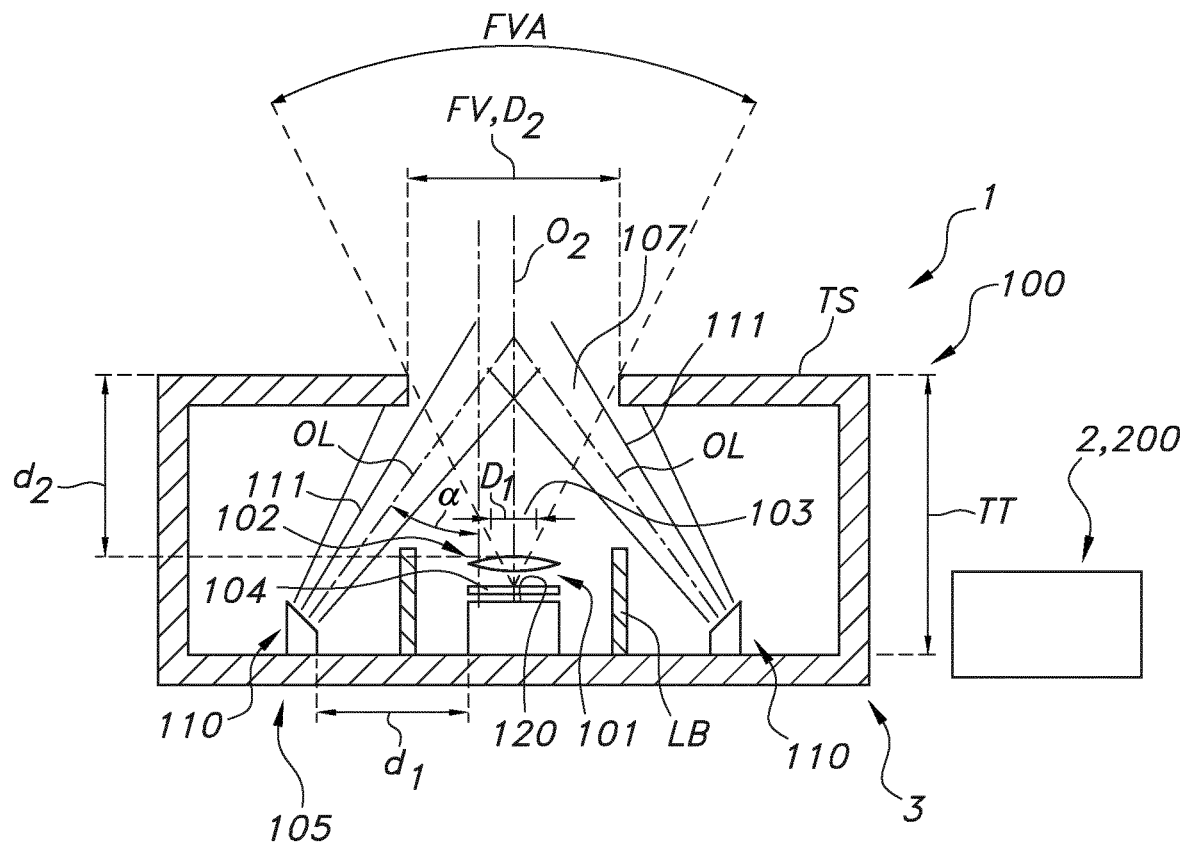
FIGS. 1a-1b schematically depict some aspects of the system.

FIG. 1a schematically depicts a system 1 comprising a sensor 100 for measuring a skin parameter (selected from one or more of the group consisting of skin gloss and skin oiliness). The sensor 100 comprises a plurality of spatially separated light sources 110 configured to provide light source light 111, and a detector 120 configured at a first distance d1 from each of the light sources 110. The sensor 100 is configured to provide the light source light 111 with optical axes OL under an angle of incidence α selected from the range of 10-80° with the skin at a second distance 2 and to detect reflected light source light 111. The sensor 100 may especially comprises at least three light sources 110 here, only two are depicted for the sake of understanding, wherein the light sources 110 are configured to provide unpolarized visible light source light 111. The first distance d1 may e.g. be selected from the range of 10-80 mm, and wherein the detector 120 is configured to detect polarized light.

The detector 120 may e.g. comprise a 2D camera 101. Further, the sensor 100 may comprises a focusing lens 102 configured upstream of the detector 120, and an aperture 103 configured upstream of the detector 120 and upstream of the focusing lens 102. The aperture 103 has a diameter D1 selected from the range of 0.1-0.8 mm. The focusing lens may e.g. be an f 5-15 mm, like 10 mm lens. Further, the system may include a second focusing lens, the combination of this lens with the first lens may provide a desired field of view and depth of focus for the overall system (see e.g. FIG. 2a). The light sources 110 are configured to provide unpolarized white light source light 111.

As indicated in FIG. 1a, the system 1 may further comprises an analysis system 2 wherein the analysis system 2 is configured to generate a corresponding skin sensor value in dependence of a sensor signal of the sensor 100.

The analysis system 2 may be comprised by a device that also comprise the sensor 100 (see also FIG. 1b), or may be comprised by a separated device. FIG. 1a also schematically depicts such embodiment, wherein the system 1 comprises the a skin care device 3, wherein the skin care device 3 comprises the sensor 100, and a second device 200 functionally coupled to the skin care device 3, wherein the second device 200 comprises the analysis system 2.

The sensor 100 includes an opening 107. This opening may especially be flat, i.e. its circumference may have an edge that is essentially flat. In this way, the sensor may be configured flat on the skin. The opening 107 may have a diameter D2 or equivalent diameter D2 which may be in the range of about 10-30 mm.

Reference O2 refers to the optical axis of the sensor 100. When the sensor 100 is configured on the skin, this axis may essentially coincide with a normal to the skin.

Reference TS indicates a top surface of the sensor. This may be a planar surface. Reference LB indicates a direct light blocker, configured to prevent that light of the light sources may reach the detector without a single reflection and/or which may reduce light reaching the detector 120 that has not been reflected by the skin but by other internal surfaces of the sensor. Reference 104 refers to a polarizer.

The axis O2 may essentially coincide with a normal to the skin.

Especially, TS may indicate a top surface of a housing 105. The top surface TS may in fact define the second distance d2 from the skin to the detector 120 or its last lens. Here, the top surface TS comprises aperture 107. The opening size of the aperture can also be indicated as field of view (FOV). The field of view is herein also indicated with reference FV. Note that the opening or aperture 107 may be circular, but may also be square or rectangular, or may have another shape. Reference FVA indicates the field of view angle. Reference TT indicates the total track, which is the distance from the aperture 107 (i.e. skin during operation) and the top side of a support hosting the light source 110, which distance is essentially the same as the distance to the top of the light source 110, as in general solid state light sources, such as LEDs, are applied. The total track may be in the range of 10-200 mm, such as in the range of range of 10-80 mm, such as e.g. in the range of 10-30 mm, or in the range of 40-200 mm, like in the range of 40-80 mm. The total track TT is larger than the second distance d2. The detector 120 and optional optics may have a height in the range of about 1-50 mm, such as 1-20 mm. As can be derived from the drawing, when the sensor 100 is configured on the skin, the second distance d2 is guaranteed. Therefore, the sensor 100 may include a distance holder, such as a housing 105 (as depicted), or optionally a housing and a separate distance holder. As indicated above, the visible light source light 111 is especially unpolarized. Hence, the light source light 111 is especially unpolarized light source light. Note that the optical axis O2 of the sensor 100 and an optical axis of the detector 120 may essentially coincide. Further, the optical axis O2 of the sensor and a net optical axis of all light sources 110 may coincide.

In general, distance d2 may be defined as the distance between an aperture that is to be position on the skin, and the detector, or its last optics, seen from the detector.

Figure 1B:
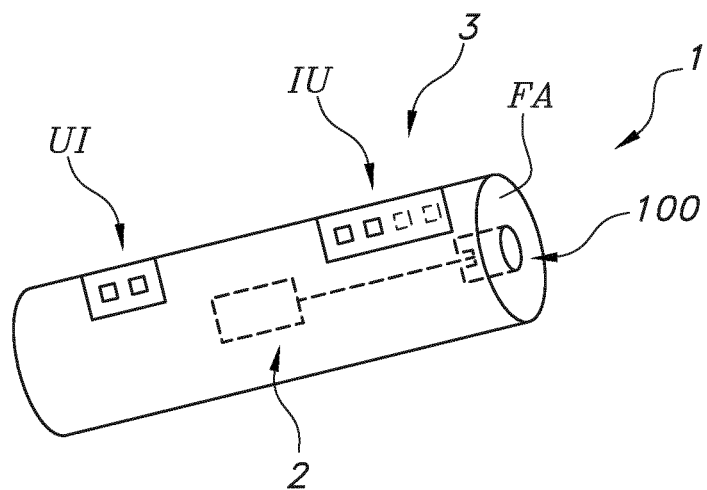

FIG. 1b schematically depicts an embodiment of the system 1, wherein the system 1 comprises a skin care device 3, such as skin cleansing device, skin rejuvenation device, wherein the skin care device 3 comprises the sensor 100 and the analysis system 2. The skin care device 3 may comprise an indication unit IU and/or also a user interface UI. Reference FA indicates a functional area, such as an area that may be used for massaging or exfoliating the skin.

Figure 2A:
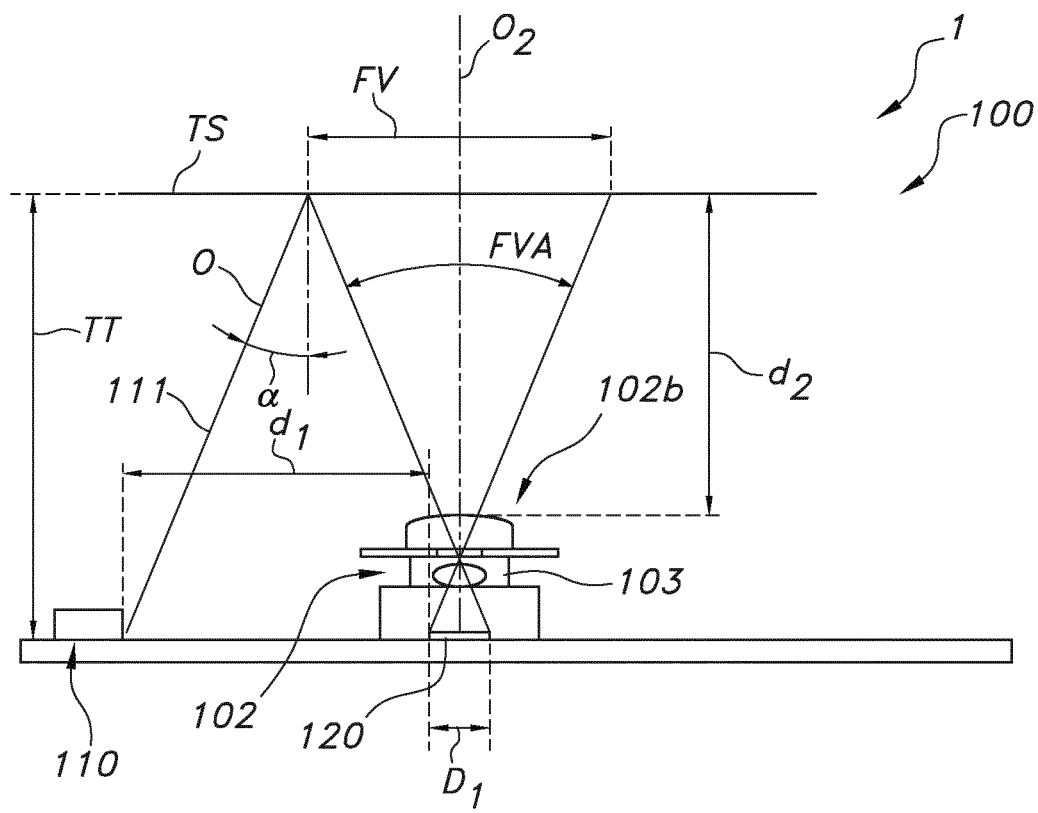
FIGS. 2a-2b show the optical layout of the system model used for simulations, and some aspects in relation to the field of view.

In order to investigate our skin gloss camera system we have used Monte Carlo ray tracing with dedicated software. The simulations calculate the photometric and radiometric quantities to perform a complete illumination and detection analysis. The schematic representation of the camera prototype and system layout is shown in FIG. 2a. FIG. 2a schematically depicts a further embodiment of the system 1. Here, an additional lens 102b is applied, configured upstream of the aperture 103. The sensor size determines the box size such that light from the corner of the box would hit the sensor at the edge for a specular reflection. We have used a black box around the sensor to prevent signals from the walls and the stop to directly hit the sensor without having seen the skin. The skin sample has been modelled using a surface having a 17% reflectivity. Part of this reflected light is reflected specularly meaning the angle of reflection is the same as the angle of incidence and part of the light is reflected diffusely meaning there is no relation whatsoever between the incoming light direction and the reflected light. The gloss property of the sample was varied in this way by choosing which part of the reflected light is specular and which is diffuse. We investigated the full range so from 100% specular (mirror) to 0% specular or 100% diffuse (Diffuse standard). In order to be able to obtain information of the glossiness of the sample, we need the specular reflection from the LED light to be able to reach the sensor surface. Therefore the previously determined box size enables us to only use meaningful distances between LED and sensor.

The LED that has been used has a color temperature of 4000 K and a CRI of 70 and has been modeled as a Lambertian surface emitter. The LED package itself has been modelled as having a 90% diffuse reflectivity. The LED die as a surface of 70% reflectivity. The PCB is modelled as having a 60% diffuse reflectivity. The walls of the housing as well as the STOP surface have been modelled as black but not a perfect black but having 5% diffuse reflectivity. The lenses are modelled having refractive indices corresponding to the N-LASF9 and the N-BK7 glass for the larger and smaller lens respectively.

Examples of power density distributions on the sensor for three different gloss values are shown in FIG. 3. The figure shows the logarithm of the grey values. As can be seen from the plots, changes in the gloss value of the sample from a reflecting mirror (100%) to a diffuse standard (0%) corresponds to changes in the magnitude of the specularly reflected light. It drops whereas the diffuse background signal increases. Basically what happens is that in the mirror case one makes an image of the LED onto the sensor surface and the image gets more and more blurred as the degree of glossiness decreases.

Figure 2B:
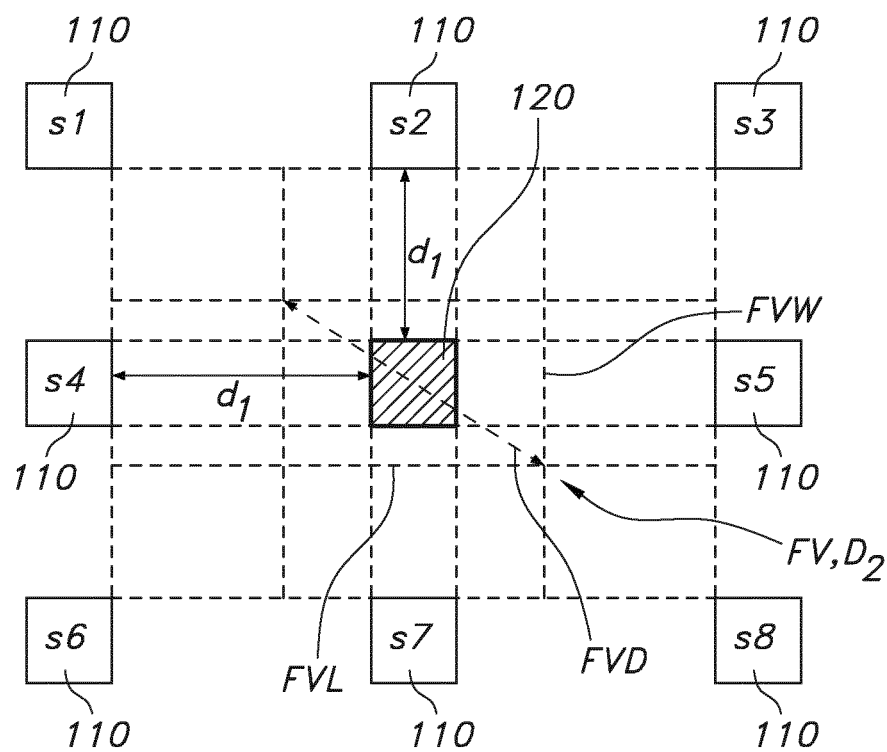

FIG. 2b schematically shows a top view (without housing), wherein the hatched rectangle in the middle indicates the detector 120. Here, a rectangular detector is applied, e.g. having a 4:3 aspect ratio. The field of view FV is the is the area at the aperture of a housing (not shown) or distance holder if applicable (not shown) that is viewable by the detector 120. Especially, this field of view, thus the aperture, is chosen such that it has the same symmetry as the detector 120, though the aperture might e.g. also have a circular symmetry. Here, the rectangular field of view FV has a length FVL and a width FVW, and a diagonal FVD. Would the field of view be circular, then there is a diameter (FVL=FVW=FWD). The light sources 110 are especially configured such that the edge to edge distance of light source 110 to detector 120 is smaller than relevant field of view dimension parallel to the respective light source 110—detector 120 first distance d1. Hence, the distances d1 of light sources 110, which are indicated with s2 and s7, are especially smaller than FVW; the distances d1 of light sources 110, which are indicated with s4 and s5, are especially smaller than FVL. Further, especially the distances d1 of light sources 110, which are indicated with s1, s, s6 and s8, are especially smaller than FVD (the diagonal).

Alternative to the edge to edge distance, also the distance of the center of the light source, such as especially a LED, to the center of the detector 120 may be applied, which should then especially be smaller than the relevant field of view dimension including 0.5 the light source size and 0.5 the detector size.

Figures 3A, 3B, 3C:
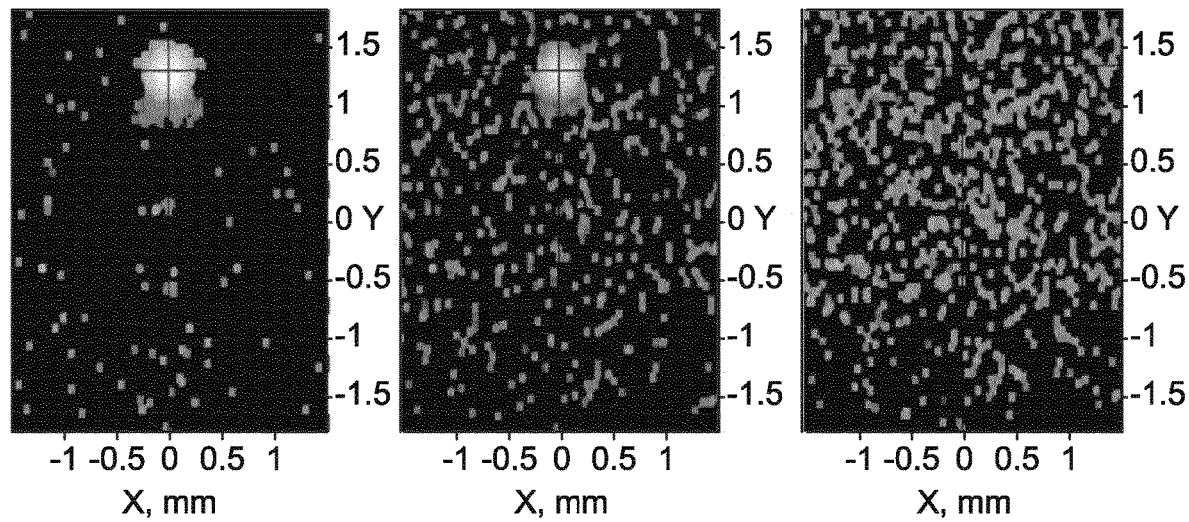
FIGS. 3a-3c show the power distribution on the sensor obtained for different gloss values where the grey values are the logarithm of the power density.

FIG. 3a shows an image provided with the system when a 100% glossy surface is measured. FIG. 3b shows an image provided with the system when a 50% glossy and 50% diffuse surface is measured. FIG. 3c shows an image provided with the system when a 100% diffuse surface is measured In FIG. 4 the information of the plots as in FIG. 3 has been represented in another way. What has been done is to integrate the power density in the rectangular are centered around the position of the specular reflection. This give us the amount of light that is reflected specularly. From the total amount of light incident on the sensor we can then calculate the power contained in the diffuse background. The ratio of these two numbers, specular power divided by the background power, is plotted in FIG. 4. As expected the ratio increases as the degree of glossiness increases. This graph implies that we can deduct the gloss value of the sample from a single image obtained with the camera prototype by using different methods such as number of pixels above a threshold weighted with intensity, slope of specular to diffuse intensity transition and ratio of specular to diffuse background in a selected region of interest. The gloss value estimated using these novel methods based on the simulations is described elsewhere herein. Details of the novel methods that we have developed for estimating the gloss value and the physical principle behind these methods is described elsewhere herein.

Figure 4:
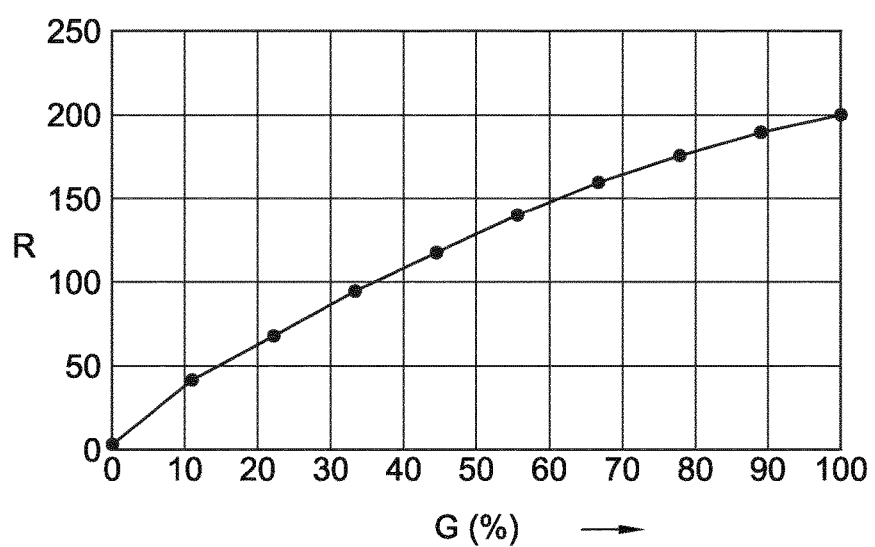
FIG. 4. The ratio between the power in the specular reflection and the power in the diffuse background as calculated from ray tracing as a function of the gloss value ranging from 0% (diffuse standard) to 100% (mirror).

In FIG. 4, on the x-axis the percent glossiness is indicated, with at 0% a diffuse surface and at the right at 100% a specular surface. On the y-axis the ratio specular to diffuse is defined (specular/diffuse).

Amongst others, below a method and system are proposed based on sequential illumination from multiple unpolarized light emitters illuminating the skin at an angle of illumination essentially equal to the Brewster's or polarization angle and using a segmented or spatially varying polarization detection.

A possible approach may be based on estimating the number of white pixels above a certain threshold as an indicator of skin gloss. However, the number of white pixels on the sensor changes as the measurement prototype/sensor is rotated. The dependence of gloss value on the rotation angle of the sensor becomes more prominent when higher values of threshold are used for estimating the number of white pixels, skin structures are present and single emitter is used for illumination. Thus the gloss characteristics of skin with spatially varying surface and structural properties could be only partially obtained using one light source in polarization sensitive camera imaging. This dependence is a critical issue as consumers will randomly position the camera sensor on to the skin and will result in non-quantitative estimation of gloss value and thus deteriorate the quality of information that can be potentially offered to the consumers.

To overcome this limitation and reduce the dependence of gloss value on the sensor rotation angle, we propose amongst others multiple unpolarized light sources (N>2) in sequential illumination and S polarized detection using a single low cost camera sensor. However in this approach, the detection of the preferred S polarization state, which is an indicator of specular reflection/gloss can only be realized only for one pair of two unpolarized light sources (either combination of U1 and U3 or combination of U2 and U4) which are diametrically opposite to each other (FIG. 5). This implies that when a polarizer with uniform polarization properties is used in the optical path for detection the maximum number of light sources that can provide the optimal polarization state is two. FIG. 5a shows a sensor in the middle, and U1-U4 indicating the unpolarized light sources. FIG. 5a shows a detection scheme and FIG. 5b shows the detection scheme assuming a uniform polarization filter.

Amongst others, it is herein proposed to use a camera system and methods for a quantitative measurement of skin gloss that is essentially independent of rotation angle of the sensor. Amongst others, a sequential illumination from more than three light sources (unpolarized) and sequential detection using a single low cost camera sensor (S polarized detection) may be used. The schematic representation of the optical layout of the camera prototype are shown in FIG. 2a.

Aspects, which were also used for a prototype, may e.g. include:
1) White light LED illumination; 2) Un-polarized illumination (Number of LEDs>3); 3) Especially an angle of incidence~54° (i.e. in the range of 50-60°) equals to the Brewster's angle; 4) LED-Sensor distance>5 mm (range 6-14 mm); 5) (Low-cost) camera sensor with a focusing lens and an aperture (stop size 0.2-0.6 mm); and 6) Segmented polarizer or spatially varying polarizer before the camera.

Image processing algorithms used for estimating the gloss value can be either based on the number of white pixels or the slope of the intensity variation along the optical axis normalized to the maximum value after flat-field correction. Other methods are also described herein.

When unpolarized light is reflected by a skin surface, the polarization properties of the reflected light depends on the angle of illumination (FIG. 6). The two orthogonal linear polarization states important for reflection and transmission are referred to as p- and s-polarization. P-polarized (from the German parallel) light has an electric field polarized parallel to the plane of incidence, while s-polarized (from the German senkrecht) light is perpendicular to this plane. Reference N indicates the normal (to a surface), reference PI indicates a plane of incidence. Further, reference SK indicates an incident surface, such as a skin surface. References S and P indicate the polarizations.

The reflected light will be unpolarized for angle of illumination equals to 0° or 90°, partially polarized (preferably S) for angles of illumination in between 0° and 90°, and plane polarized (S) for one angle of illumination equals to the polarization angle or Brewster's angle.

The angle of incidence (0° and 90°,) at which the reflection coefficient for light which has electric field parallel to the plane of incidence (P) goes to zero and the reflected light at that angle is linearly polarized with its electric field vectors perpendicular to the plane of incidence (S) is called the polarizing angle or the Brewster angle. The polarizing angle or the Brewster angle ($\theta_B$) can be calculated based on the Fresnel's equations. The Fresnel equations predict that light with the p polarization (electric field polarized in the same plane as the incident ray and the surface normal) will not be reflected if the angle of incidence is $\theta_B=1/\tan(n_2/n_1)$, wherein $n_1$ is the refractive index of the initial medium through which the light propagates (the "incident medium"), and $n_2$ is the index of the other medium. For a glass medium ($n_2 \approx 1.5$) in air ($n_1 \approx 1$), Brewster's angle for visible light is approximately 56°. For the optical lay-out as disclosed in this invention, the light is incident at the air-skin interface and the Brewster's angle is approximately 54°. The preferred range is 50-60°).

Therefore, in embodiments a segmented (for lower number of emitters up to four to eight) or spatially varying polarizer (for higher number of emitters for instance above 12) in the detection path can be used. Especially, the number of segments equals to the number of emitters.

Figure 7:
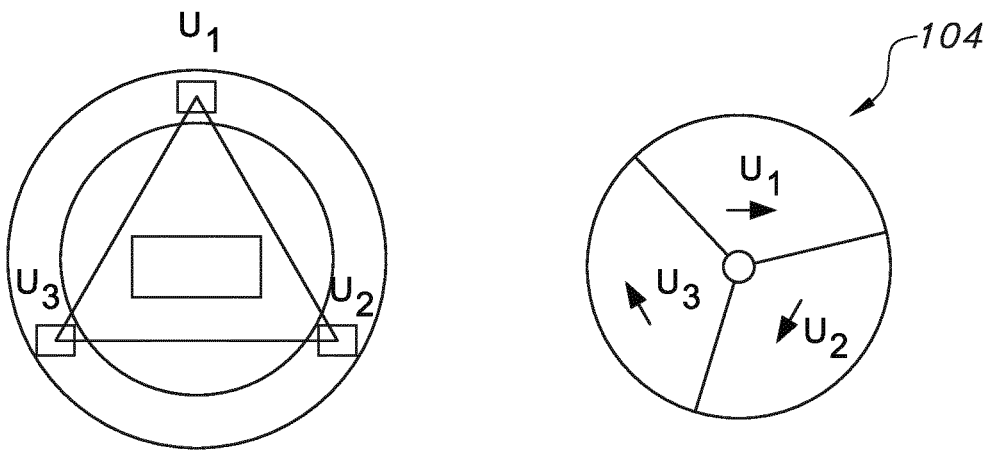
FIG. 7: Schematic representation of the polarization schemes for illumination and detection for minimizing the dependence of gloss value on sensor rotation.
Figure 7:
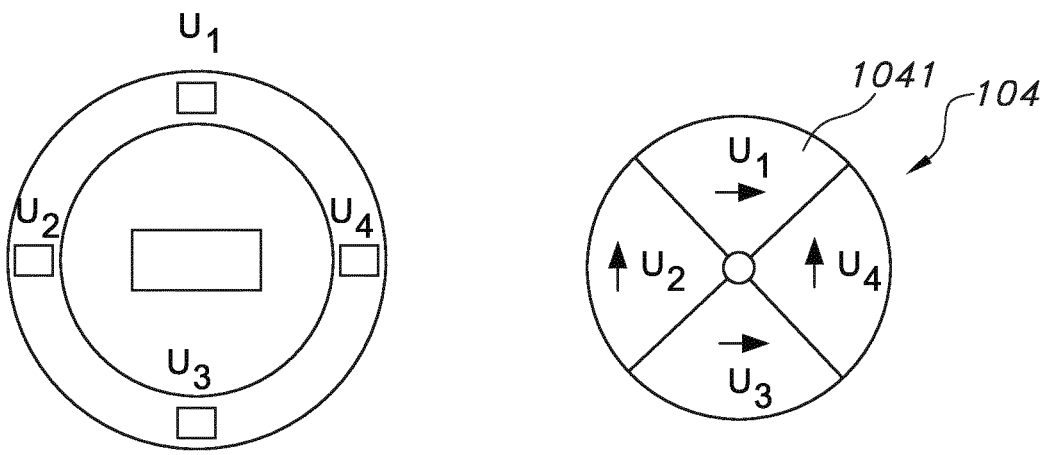

When the angle of illumination is between 0-90°, the detection of partially polarized (preferably S) reflected specular light which is a measure of gloss can be enhanced by filtering in this component using an S polarizer before the camera. In the case of illumination scheme using multiple light sources, segmented polarizer or spatially varying polarizer as shown in FIG. 7 can be used. This implies that when four emitters are used for illumination, the orientation of the polarizer before the sensor for the pair of light sources (U2 and U4), has to be orthogonal (H) to the orientation of the polarizer (V) that is used in the optical path for the light detected from $U_1$ and $U_3$. These segments can be cut from a standard low-cost polarization sheet and can be placed in the respective orientation by rotating individual segments for making a segmented polarizer. Reference 104 indicates a polarizer. Further, reference 1041 indicates a segmented polarizer.

Figure 8A:
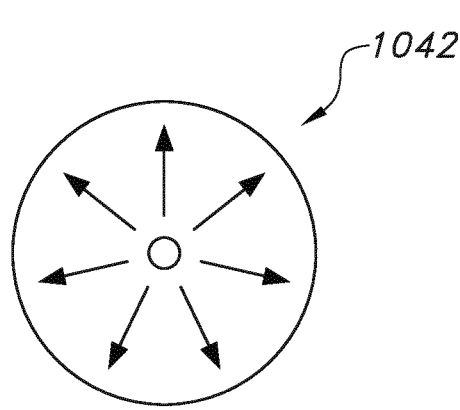
FIGS. 8a-b schematically depict some embodiments of spatially varying polarization filters or retarders.
Figure 8B:
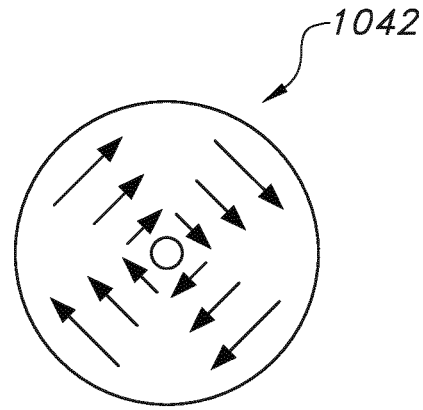

FIGS. 8a-b indicate spatially varying polarizers 1042, which are azimuthal or radially varying, respectively The segmented polarizer can be placed in the optical path for detection or can also be imprinted on the camera sensor itself by fabricating wire grid polarizers using standard CMOS process. High-speed polarization image sensor with a pixel size of 6 μm has been already reported for polarization mapping consists of 4 sub-pixels with a reference and three grid-covered pixels with an orientation of 0°, 45° and 90°.

Figure 9:
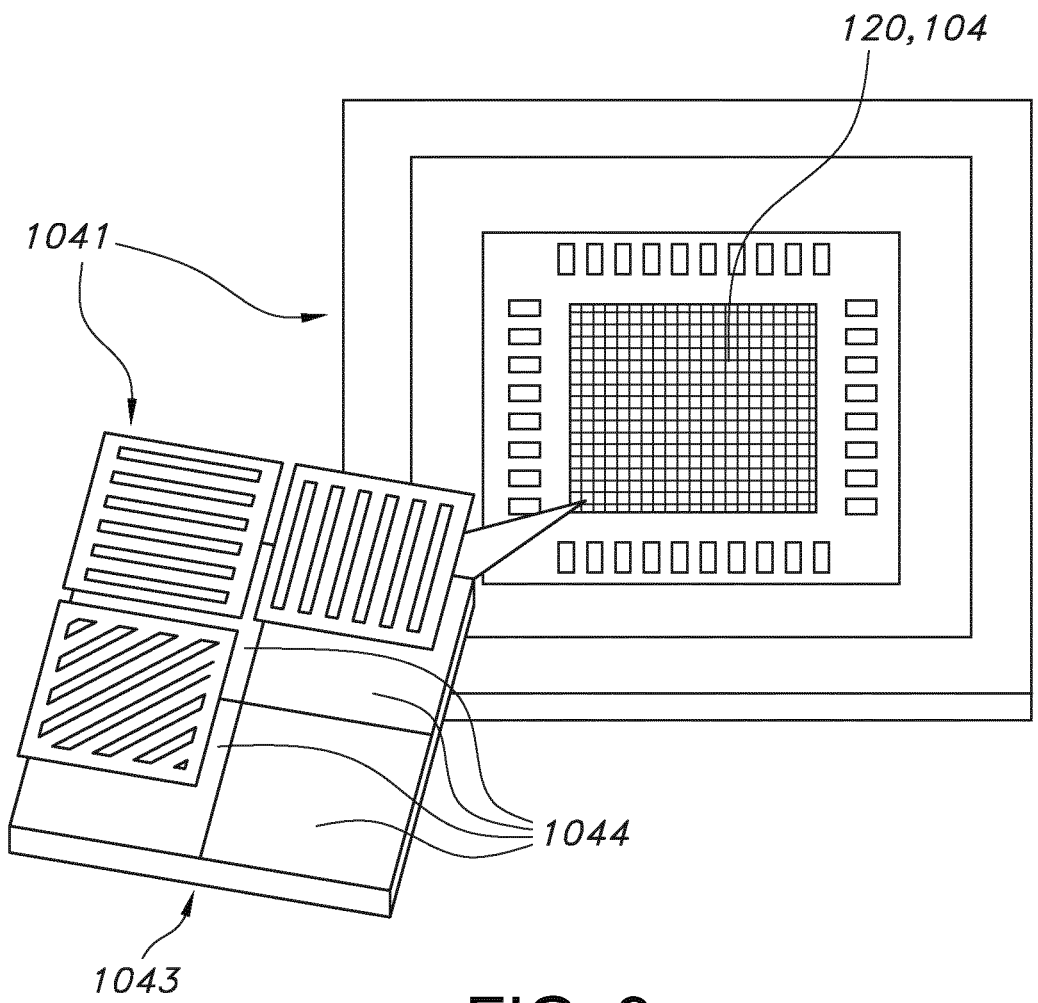
FIG. 9: Pattern of the nanowire polarization filter array used for a CMOS polarization image sensor consists of 4 sub-pixels with a reference and three grid-covered pixels with an orientation of 0°, 45° and 90°.

FIG. 9 schematically depicts an embodiment of a segmented polarizer 1041 comprises a pixelated wire grid polarizer 1043 with two sets of two pixels 1044 having polarization orientations perpendicular to each other.

As indicated above, the measurement of gloss characteristics of skin with spatially varying surface and structural properties using an optical sensor may depend on the sensor rotation angle when one or two light sources are used. This could result in non-quantitative estimation of gloss value and thus deteriorate the quality of gloss information that can be potentially offered to the consumers.

Hence, herein also systems and methods for quantitative measurement of skin gloss that is less dependent on the rotation angle of the sensor are proposed. The proposed invention may alternatively or additionally be based on using sequential illumination and detection using more than three light sources (unpolarized illumination) and a camera sensor (polarized detection).

Amongst others, we analyzed the changes in number of white pixels versus the rotation angle of the sensor in polarization camera imaging set-up. Amongst others, we observe that the dependence of gloss value on the rotation angle of the sensor becomes more prominent at high threshold, when structure are present and when one emitter is used for illumination.

Hence, amongst others, it is herein proposed to use camera systems and methods for quantitative measurement of skin gloss that is (are) less dependent on the rotation angle of the sensor. The proposed invention—may in embodiments amongst others—be based on using sequential illumination from more than three light sources (unpolarized illumination) and sequential detection using a single low cost camera sensor (polarized detection). The gloss value is estimated based on the average number of pixels estimated from the multiple independent images taken along different directions. The schematic representation of the optical layout of the camera prototype are shown in FIG. 2a. The image processing method (algorithms) used for estimating the gloss value can be either based on the number of white pixels or the slope of the intensity variation along the optical axis normalized to the maximum value after flat-field correction, though other options may also be possible (see also below).

Aspects, which were also used for a prototype, may e.g. include: 1) white light LED illumination; 2) un-polarized sequential illumination with multiple emitters (Number of LEDs>3); 3) angle of incidence especially >45° (especially in general in the range) 40-80°; 4) LED-Sensor distance>5 mm (range 6-14 mm); 5) (Low-cost) camera sensor with a focusing lens and an aperture (stop size 0.2-0.6 mm); 6) Polarizer before the camera.

We have investigated the dependence of gloss value (Number of white pixels above a certain threshold) on the rotation angle of sensor (0-360° in steps of 30°. Measurements were performed using the camera prototype using one and two emitters with sequential illumination.

Spectralon (Diffuse standard with uniform optical properties);
Ex-vivo Skin (for performing controlled experiments); and
In-vivo Skin (Forehead, Skin type II).

Figure 10:
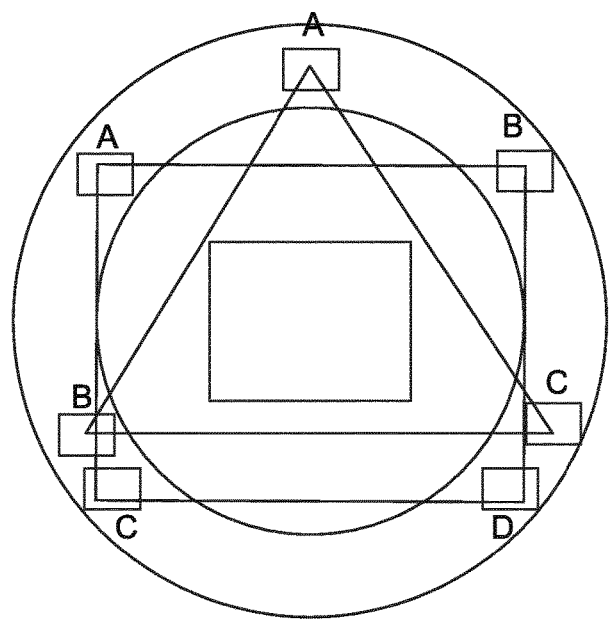
FIG. 10: Schematic representation of a possible polarization scheme for illumination and detection.

Based on the experimental data measured on Spectralon, ex-vivo skin and in-vivo we exemplify that the underestimation of the gloss content resulting from the rotation related effects associated with the use of using single emitter could be minimized by using sequential illumination employing more than three emitters (triangular configuration for N=3 and rectangular configuration for N=4 etc.) that are symmetrically placed in a ring illumination configuration (FIG. 10). When multiple emitters are used simultaneously, the gloss value depends on the rotation angle, effect predominantly contributed by the number of white pixels in the regions where the intensity distributions from multiple emitters overlap. Herein, A, B, and C indicate light sources, which are arranged in a ring configuration.

Figure 11:
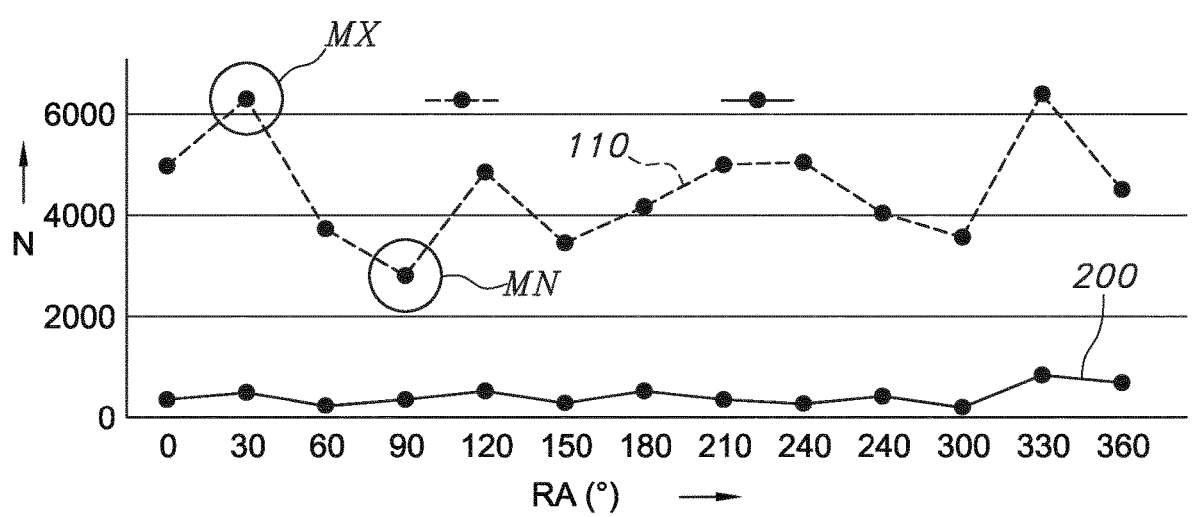
FIG. 11: The variation of number of white pixels measured in-vivo as a function of rotation angle of the sensor for different threshold.

To quantify the dependence of gloss on the sensor rotation angle, the number of white pixels were estimated as a function of sensor rotation angle for different threshold (FIG. 11). FIG. 11 shows on the x-axis the rotation angle RA of the sensor and the y-axis indicates the number N of white pixels (in arbitrary units). The number of pixels POL_L are displayed as function of angles for a number of thresholds, wherein 110 indicates a threshold of a value of 110 and 200 indicates a threshold of a value 200. The references MX and MN indicate a maximum and minimum, respectively.

For a given threshold, the dependence of gloss on rotation angle is expressed in terms of maximum relative difference in number of pixels: ($\Delta$Gloss)=(max-min)/(mean (max,min)).

The following conclusions can be made based on these experiments:
the number of pixels estimated from the Spectralon with uniform optical properties showed less dependence on the rotation angle of the sensor;
the number of pixels estimated from ex-vivo and in-vivo skin measurements showed dependence on the rotation angle;
this dependence of gloss value on rotation angle is resulting from the non-uniformity of the skin structural and surface properties. This dependence on angle becomes more prominent when skin structures are present and in particular after cleansing; and
the dependence on the sensor rotation angle can be minimized using multiple illumination sources in comparison to single emitter. This dependence is further reduced when multiple emitters are used sequentially (L_R) than simultaneously (L, R):

$\Delta$Gloss (Unpol)(L_R) $\Delta$Gloss (Unpol)(L, R)<$\Delta$ Gloss (Unpol)L, $\Delta$Gloss (Unpol)R and/or
$\Delta$Gloss (Pol)(L_R)<$\Delta$Gloss (Pol)(L, R)<$\Delta$ Gloss (Pol)L, $\Delta$ Gloss (Pol)R Here,
L: Single unpolarized emitter from Left side;
R: Single unpolarized emitter from Right side;
L, R: 2 emitters (L and R) are used simultaneously and single image is captured; and
L_R: 2 emitters (L and R) are used sequentially and gloss value is estimated based on the average value (L and R emitters are positioned diametrically opposite to each other in a ring-configuration).

The results are summarized in below table:

| conditions | Spectralon maximum relative change in no. of pixels due to rotation (0-360) | Ex vivo maximum relative change in no. of pixels due to rotation (0-180) | skin type 2 (before cleansing) maximum relative change in no. of pixels due to rotation (0-360) | skin type 2 (after cleansing) maximum relative change in no. of pixels due to rotation (0-360) |
|---|---|---|---|---|
| unpol_R | 0.03 | 1.29 | 0.57 | 1.87 |
| unpol_L | 0.05 | 1.48 | 0.62 | 1.62 |
| unpol_LR | 0.01 | 0.96 | 0.42 | 1.81 |
| unpol_L_R | | | 0.33 | 1.65 |
| pol_R | 0.05 | 2 | 0.94 | 1.81 |
| pol_L | 0.1 | 2 | 1.29 | 2.0 |
| pol_LR | 0.02 | 2 | 0.85 | 1.83 |
| pol_L_R | | | 0.77 | 1.81 |

Hence, amongst others skin gloss measurement systems and methods using sequential illumination from more than three light sources (unpolarized illumination, equal-angular separation) and single low cost camera sensor (polarized detection) to minimize the dependence of gloss value on the sensor orientation are herein provided.

Figure 12:
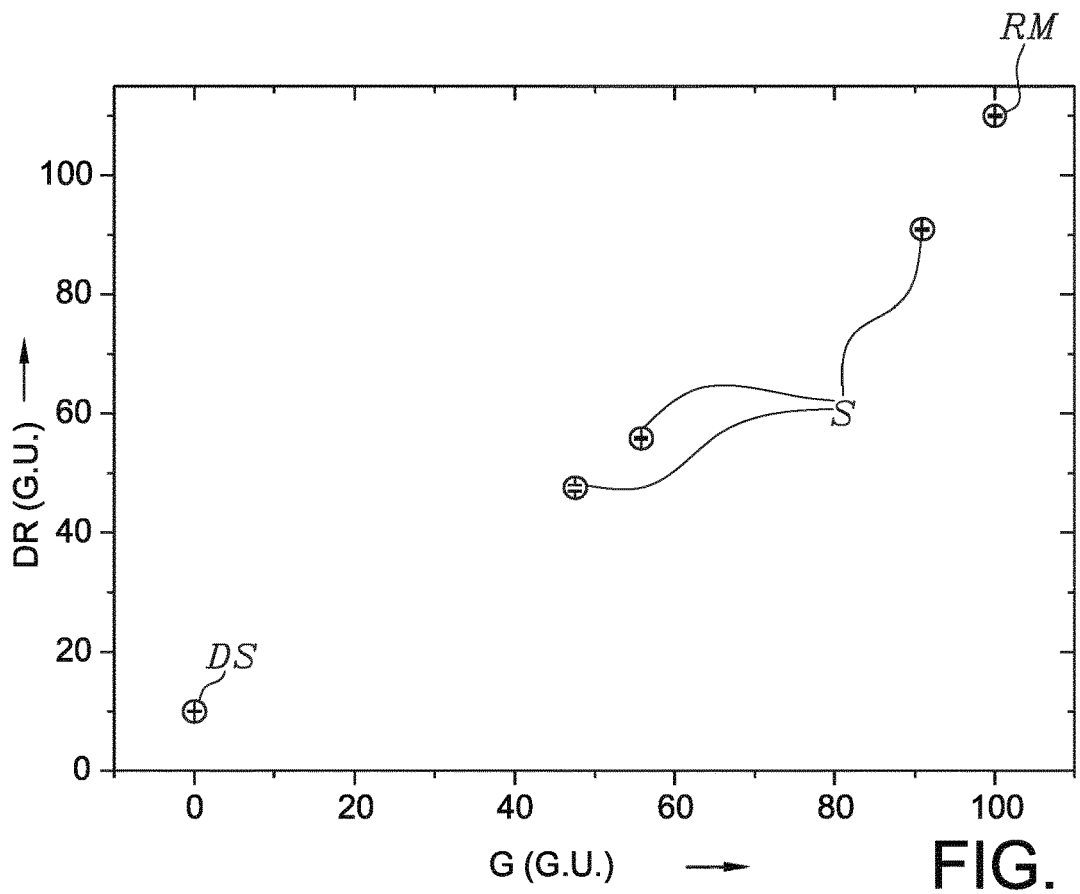
FIG. 12. Calibration of the professional gloss meter based on measurements on calibration standards, diffuse standard and reflecting mirror.

Below, we report on the experiments performed on calibration samples (mirror, calibration tiles, gloss papers, diffuse standard) with a range of gloss values from 0 to 100 gloss units. We compare the gloss values measured with the camera to other professional devices known in the art). FIG. 12 shows the device reading DR in GU units, with DS indicating the diffuse standard, RM indicating a reflective mirror, and S indicated gloss calibration standards. On the x-axis the gloss in GU of calibration standards is indicated.

Measurements were performed using professional industrial gloss meter Gardner (G85) to define a measurement scale ranging from 0 to 100 Gloss Units (GU). The performance and linearity of the professional gloss meter (Gardner 85) in the higher range of gloss units were measured using three highly polished reference black glass standards (Novo Gloss) with a defined refractive index of known reference gloss units of 50, 60, 90 GU. They were used as 'calibration tiles' or 'calibration standards'. There is no such a material that provides wide range of gloss values with the same surface properties and with sufficient number of samples. The first calibration tiles cover medium-high gloss values, while the gloss papers covers low gloss values. Therefore we have used gloss papers with a range of gloss values in the lower range of gloss units after calibration of the device using these calibration tiles. These calibration standards have assigned gloss unit values for angle of measurement and traceable to BIN standard for Material Research. We observed good correlation between the gloss value measured with Garnder 85 and gloss reference value of the calibration gloss standards. We have performed additional experiments on a mirror and diffuse standard to establish an upper point calibration of 100 on a mirror and with the lower end point established at 0 on a diffuse standard. We observed an offset of 10 GU on mirror and diffuse standard. The measurements performed with other angle of illumination such as 20° and 65° in the Gardner device were not able to measure in a broad range of 0 to 100 GU and therefore we have used the specific angle of illumination of 85° as the reference for the following measurements.

Figure 13:
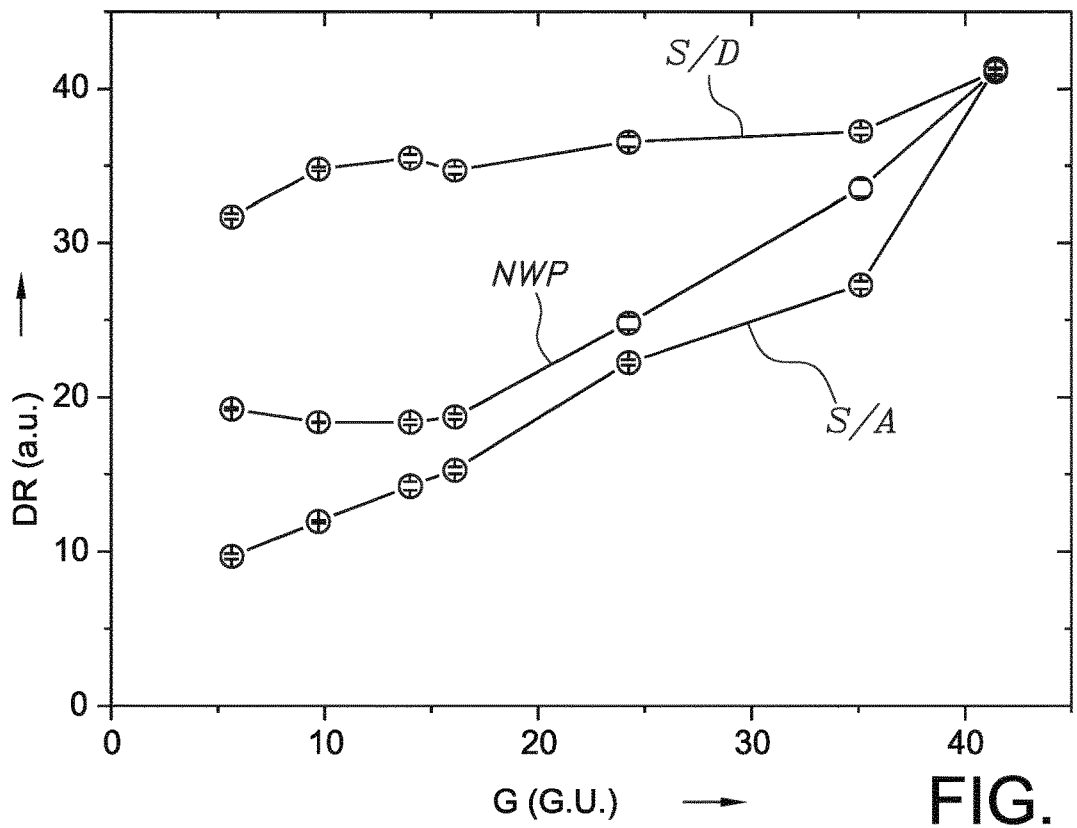
FIG. 13: Comparison of different methods (Angle, S/D ratio, Number of weighted pixels) for estimating gloss value in the lower gloss range.
Figure 14:
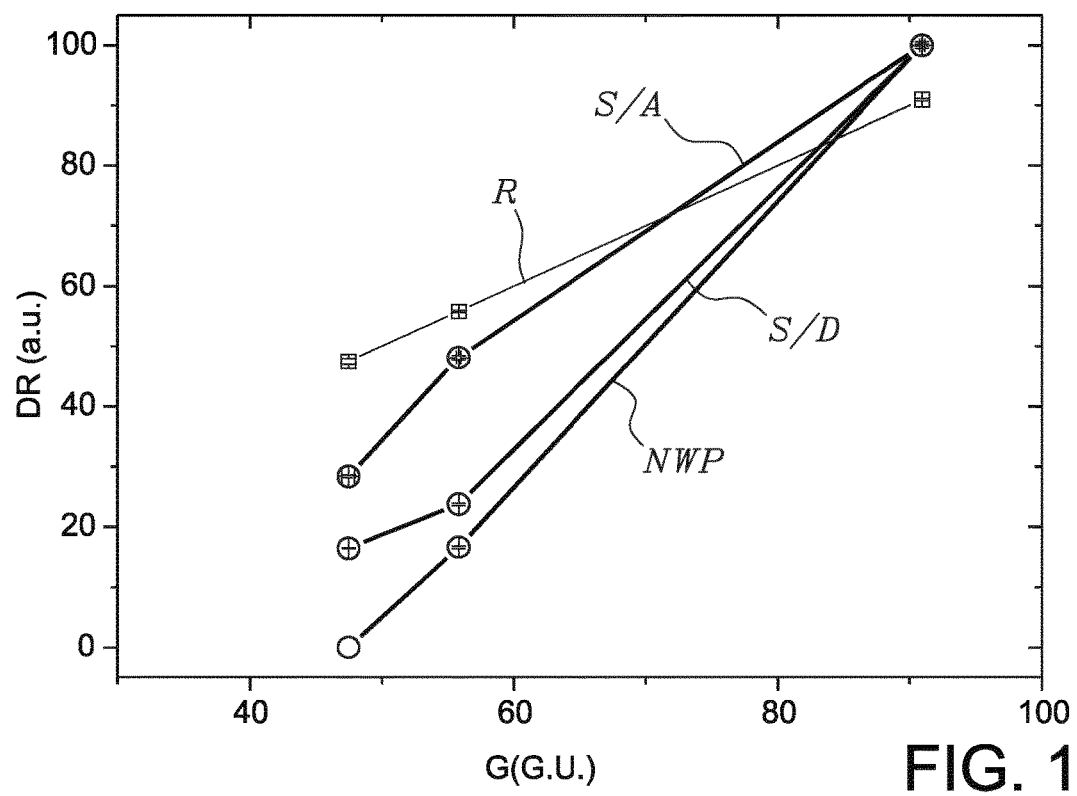
FIG. 14: Comparison of different methods (Angle, S/D ratio, Number of weighted pixels) for estimating gloss value in the higher gloss range.

The performance and linearity of the camera prototype and algorithms in measuring gloss in the low and high gloss range using gloss papers (FIG. 13) and calibration tiles (FIG. 14) respectively. The description of different methods used for estimating gloss based on the camera images and the definition of flat-filed correction can be found in Chapter 6. The gloss units measured with professional device, Gardner 85 is used as the reference value in the horizontal axis. The camera readings are normalized to the maximum value. We observe that the measurement accuracy of different methods depends on the gloss range of the samples. For lower gloss values, the measurement accuracy of slope and number of weighted pixels are higher than that of specular to diffuse ratio approach. In the case of samples with high gloss values number of weighted pixels and specular to diffuse ratio are superior as compared to the slope/angle method. These observations are consistent with the results of simulations. FIG. 13 shows on the x-axis the gloss units and on the y-axis the device reading in arbitrary units. Reference S/D indicates the slope/diffuse ratio related values; S/A indicates the slope/angle ratio related values; and NWP indicates the number of weighted pixels related value. FIG. 14 uses the same references as in FIG. 13 for the different curves; in addition, reference R indicates reference gloss units.

Currently, different angles of illumination are used depending on the gloss levels. An 85° angle of incidence (AOI) gloss meter is more sensitive to differences in gloss below 10 GU @ 60° whereas a 20° AOI has higher resolution on high gloss coatings above 70 GU @ 60°. This indicates that one camera device with different algorithms approaches can be used for measuring the gloss value in the range of 0 to 100 GU without any hardware modification and reasonably good accuracy can be obtained for all samples using the number of weighted pixels method.

The gloss levels of a sample was measured and the performance of our method on calibration standards with other professional gloss meters was evaluated. The measurement accuracy of the surface properties of both calibration tiles and gloss papers are uniform. The results can be different when measurements are performed on skin with anticipated non-uniform surface properties and anticipated low gloss values.

In addition to this, the measurement of skin gloss using the camera can be influenced by a number of factors, for example, skin color, the extend of skin doming depending on the applied pressure and the amount of sebum, sweat etc. on the skin surface. Skin color probably will give only an effect of intensity difference in blue, green or red channels and can be compensated by auto intensity correction in a final system. Detectable differences in gloss depend on the gloss level of the sample and the relevance of these detectable differences depend on how many units of gloss would subjectively be perceived as significantly different. When measuring at 60° these detectable differences depend on the gloss level of the sample, for instance 3.0 GU difference measured on a very matt surface (perhaps 5 GU), would be seen by the human eye but on a higher gloss coating (perhaps 60 GU) the difference would be very difficult to notice.

Below, some possible (pre)processing steps are described, based on RGB to grayscale imaging and flat field correction), which can be used as preprocessing steps for the methods described below (or above). It is assumed that obtained images are not saturated. Saturated images enhance overall intensities of an image and thus not relevant (background) information might be taking into account.

Every camera capture provides four images obtained by four unpolarized light sources, which are positioned at the bottom right—BR, bottom left—BL, top left—TL and top right—TR. These images then used to perform spatial averaging and to minimize the dependence between glossiness value and a rotation of a sensor. RGB to grayscale: The image from the SensorTech camera is a 24 bit RGB image. Each color has 8 bits. The color value for each pixel in the RGB image is a 24 bit value. For each pixel the tree color intensities can be derived by using portions of the 24 bit number (Bit 0-7 represent BLUE (B), Bit 8-15 represent GREEN (G), Bit 16-23 represent RED (R)). A grayscale image is an average information obtained from R, G and B channels and when checking an RGB image for saturation, the individual channels should be checked. In the algorithms implemented by LabVIEW, a grayscale image is obtained by summation of three (R, G and B) channels, i.e. the maximum intensity of an image can be 3×255=765.

Flat field correction: The goal of flat field correction (FFC) is to remove artifacts from an image caused by variations in pixel to pixel sensitivity of the camera and an overall intensity distortions in the optical path. Also, we use FFC to compensate for a gradient change in pixel-intensities over an image as a result of unpolarized light. In order to perform FFC, a reference image—diffuse standard such as "spectralon" is used. Since we have multiple light sources on the SensorTech camera, different reference images are taken, i.e. FFC is done for each emitter separately.

The flat field correction (FFC) of an image is done by dividing an image by the reference image (spectralon) and then by multiplying each pixel with the average pixel intensity of the reference image.

Below, some methods are described that can be used for (quantitative) measurements.

Number of pixels above threshold: this method is based on the fact that specular reflected light appears brighter in an image than the diffuse background. It is important that images are not saturated: 1) we use images from the 4 unpolarized light sources of the camera (BR, TL, BL and TR). Each image is processed separately; 2) convert an image from RGB to grayscale; 3) apply FFC to the grayscale image; 4) determine maximum pixel intensity in the image; 5) count the number of pixels with an intensity that is higher and lower than half the maximum intensity; 6) Result is: (#pixels higher)/(#pixels lower); 7) average=(#pixels higher)/(#pixels lower result of 4 images). With more or less light sources, instead of 4 images the n images may be used, with n referring to the number of light sources.

Slope (angle) calculation: this method utilizes the slope (angle) of the intensity distribution in a region of interest defined in a window around the specular to diffuse transition in the direction of optical axis and uses unpolarized light sources. A perfect mirror would give 100% specular reflection of an emitter concentrated on a small region on the sensor with zero background (noise) whereas a perfect diffuse standard gives nearly uniform intensity distribution on the sensor after FFC. The slope (angle) gives an indication of how fast the intensity drops as a function of distance along the optical axis. The following actions may be included (see also FIG. 15):

1. Each of four images obtained from unpolarized light sources of the camera (BR, TL, BL and TR) is processed separately;
2. Convert an image from RGB to grayscale;
3. Downsample the image with a factor 8 to remove backwards scattered light caused by a skin structure. Apply a median filter with a kernel size of 15 to further remove any skin structures and upsample the image again towards the original size;
4. Now we will search the hotspot intensity of the image. It is represented by a region with the maximum intensity. This is done by the following steps:
    a. Search for the maximum intensity in a 16× downsampled image;
    b. Threshold the image with this intensity;
    c. Create a binary image (0=below threshold, 1=above threshold);
    d. Use 8 connectivity to create BLOBs (Binary Large Object);
    e. Get the center of mass of the largest BLOB;
5. Define a line between the defined hotspot intensity and the center of the image.
6. Create (#160) rectangles (width 75, height 50) with the centers of the rectangle evenly divided over the line;
7. If a flat field correction is applied then repeat the steps 5, 6, 7 on the references image and divide by the results of the flat field;
8. Introduce results in and X, Y coordinates, where X corresponds to the range of [1,160] and Y is the average intensity.

Specified parameters (steps 6-8) were selected with respect to the images obtained by the current system. It is possible that these parameters may require additional tuning for images acquired by other devices.

9. Get the average intensity in each rectangle;
10. If the maximum of that graph is not a X=1 then remove the part until the maximum value of Y. Divide the remaining graph into 3 part;
11. Calculate the slope in the graph over the first graph. This is always a negative number.
    a. High specular reflection should result in a high negative number.
    b. Diffuse reflection should result in low negative numbers.
12. Average the result of slope obtained for four images.

Figure 15A:
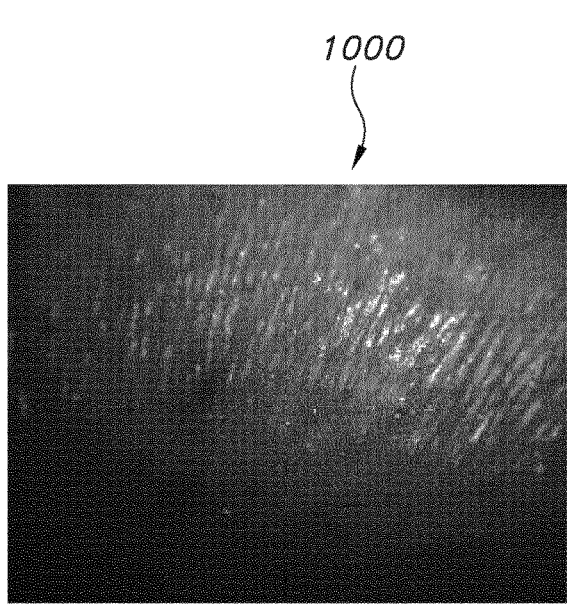
FIGS. 15a-d: Illustration of image processing steps for estimating gloss based on slope (angle).
Figure 15B:
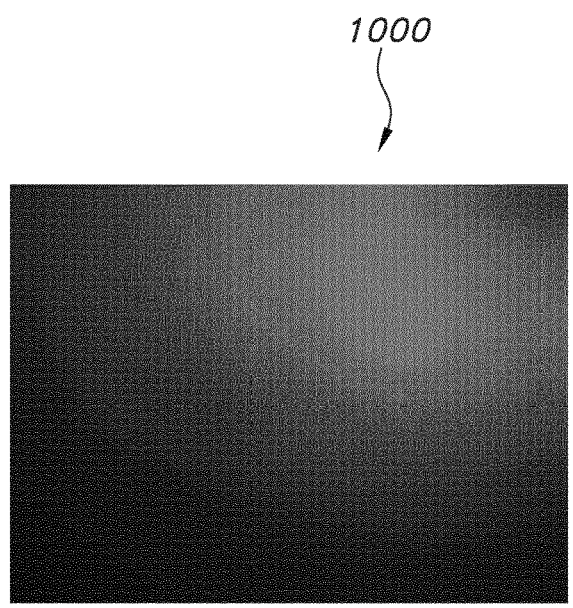
Figure 15C:
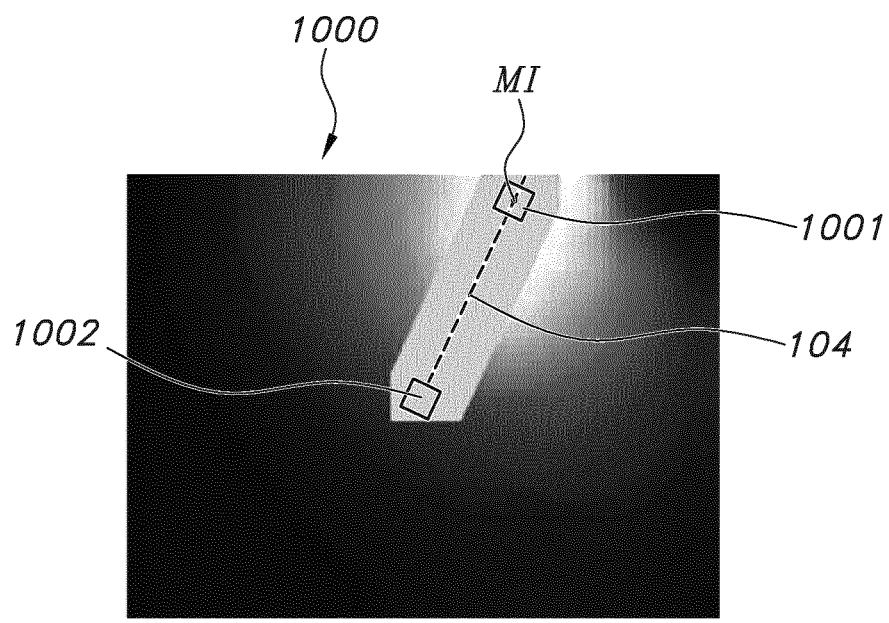
Figure 15D:
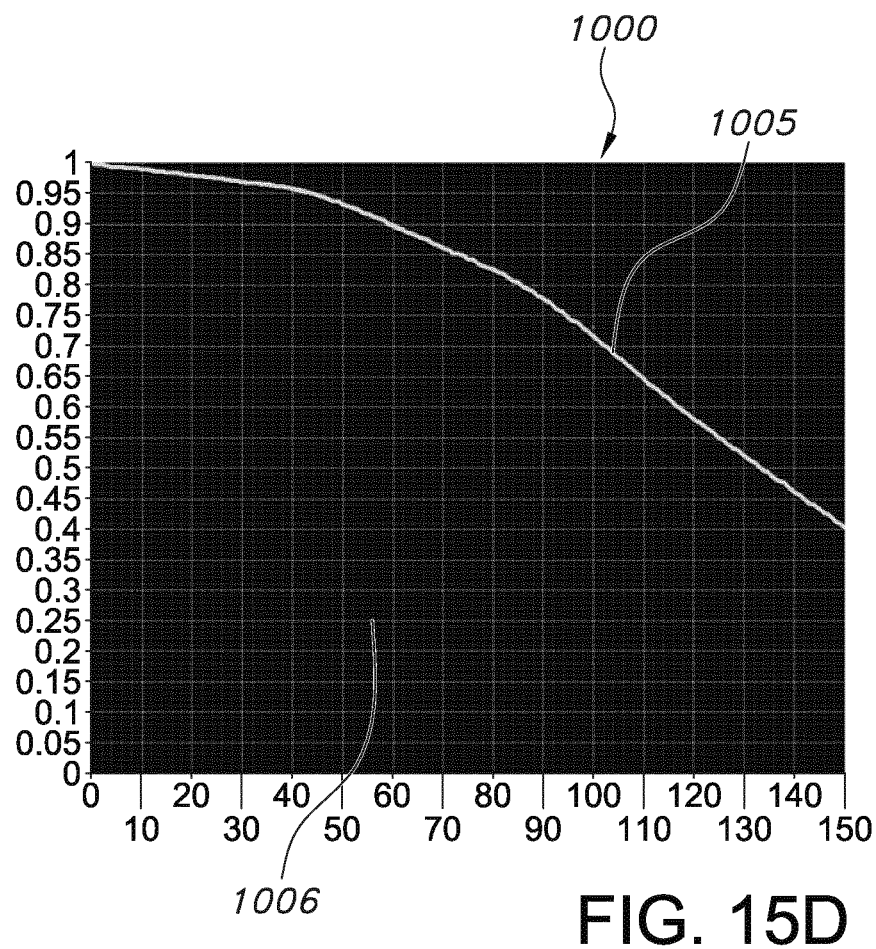

FIGS. 15*a*-15*d* schematically depict various images of the skin, where FIG. 15*a* shows an unprocessed image; FIG. 15*b* shows a processed image, such as after FFC. FIG. 15*c* shows an area with maximum intensity MI, which area is indicated with reference 1001. Reference 104 indicates a line connecting the first area 1001 and the second area 1002, which is configured at some distance. Moving from the first area 1001 to the second area 1002 along line 104 may be essentially the same as moving the window along the optical axis. FIG. 15*d* shows the intensity profile along this line. The slope 1005 and/or the area 1006 under the curve may be used as measure for the skin parameter.

Ratio specular to diffuse intensity: the direct reflected light (guided by a mirror in the same angle into the reflection channel) and the diffuse reflected (scattered) light are received in two separate measurement channels. The scattered/diffuse reflected light is measured at 0° (completely vertically above the measured surface) under the assumption that light is scattered in the same way over all degrees (diffuse channel). These specular and diffuse components are spatially separated but detected on the same sensor plane and use broadband wavelength illumination and a broad range of angle of illumination and detection. The method is based on calculating the ratio of intensity in a region of interest around the specular spot to that of diffuse background. These regions of interest are similar to areas used for estimating gloss based on slope (angle). Thus, the ratio of specular to diffuse intensity gives maximum values for samples with high gloss values such as mirror (~1).

Especially, in this method, averaged intensities of an area with the highest reflection compared to averaged intensities of an area of diffuse reflection.

1. Over the area of the rectangle with the highest specular reflection, averaged intensities are calculated;
2. Similarly, over the area of the rectangle with the maximum diffuse reflection, averaged intensities are calculated; and
3. The calculated ratio is the ratio of the intensities (step 1/step 2)

Polarization different imaging method (SAMBA analogous method): this method may use polarized channel information in addition to the unpolarized illumination channel. Skin was illuminated by polarized and unpolarized light sequentially and was detected using a polarized camera sensor. Basically, the measurement principle of this method is based on polarization-difference imaging and is similar to the one used in the professional gloss measuring device such as SAMBA. Herein, however, we use unpolarized light and a polarization filter. For our calculations in the SAMBA analogous method, we use polarized and unpolarized light sources. Unpolarized light sources have specular and diffuse components, while polarized light has only diffuse components. In order to get the specular component, the polarized image is subtracted from the unpolarized image.

1. The images from the pol_BR and pol_TL are processed together with the images of unpol_BR and unpol_TL.
2. Convert the image from RGB to grayscale.
3. Apply FFC to the grayscale image.
4. For further processing, we transform an image through its symmetry, i.e. the maximum reflection should be on the top right (TR). pol_BR and unpol_BR images are transformed through the horizontal symmetry, while pol_TL and unpol_TL are transformed through the vertical symmetry.
5. For each four images, an average intensity is calculated within 200×200 rectangle, which is located in the center of the image. The rectangle is selected so that there is only a diffuse reflection. With these intensity-values, it is possible to compensate for light intensity between the images. Size of the rectangle is predefined for the current system.
6. Calculate 2 ratios
    a. Ratio_BR=intensity pol_BR/intensity unpol_BR
    b. Ration TL=intensity pol_TL/intensity unpol_TL.
7. Divide the unpolarized images by their ratios.
8. Add polarized images, resulting in only 1 polarized image
9. Add unpolarized images, resulting in only 1 unpolarized image.
10. Subtract: Unpolarized−Polarized.
11. Calculate the mean intensity and its standard deviation over the entire resulting image.
12. Samba result mean/stdev.

Average size of the BLOB and maximum size of the BLOB: This method is based on the average size and maximum size of the BLOB (Binary Large Object) found in the image and is more relevant to quantify oily related skin characteristics than gloss. The interplay between skin gloss and oiliness needs to still be thoroughly understood. A BLOB can be seen as a group of pixels, next to each other, with the same characteristics. The intensity of pixels should be above a certain level. The method is based on the visual appearance of oil in the image. The following steps may be executed:
1. We use only images from unpolarized light (BR, TL, BL and TR).
2. Convert the image from RGB to grayscale.
3. Apply FFC to the grayscale image.
4. Determine maximum pixel intensity in the image.
    a. Threshold the image with e.g. 80%, or 90%, or 95% of the maximum value. And create a binary image (Above threshold=1; Below threshold=0)
5. Calculate the BLOBs using 8 connectivity.
6. Calculate the average size over all the BLOBs.
7. Calculate the maximum BLOB size.
8. Calculate mean values over the 4 images (obtained with four light sources that are placed in the ring configuration).

Number of pixels above the threshold: This method is based on differences in intensities of specular and diffuse reflected lights. Specular reflection is brighter and therefore can be used to quantify glossiness after image thresholding. Here we make a use of a threshold range to facilitate a better discrimination is skin color as well as to create more sensitive method to account for additional information when no FFC is performed. This information can be discarded when only intensities of pixels above the specified threshold are considered. The main disadvantage of this algorithm is that thresholds have to be tuned for particular cases.
1. Four images (BR, TL, BL and TR) are processed separately
2. For each such an image: R, G and B channels are flat field corrected by R, G and B channels respectively of the reference image using Spectralon.
3. Use multiple thresholds {110, . . . 180, . . . , 220} for the corrected B channel and {120} for R and G corrected channels to threshold an image.
4. Count number of pixels with intensities above a selected threshold
5. Resulted number of pixels is obtained by averaging number of pixels calculated for each BR, TL, BL and TR images.

Weighted number of pixels above the threshold: This method is also based on differences in the intensity of specular and diffuse reflected. We select certain RGB intensities by thresholding an image and based on that perform steps as presented below. All the pixels, above a certain threshold, get the same value (1) independently from an actual intensity levels of the pixels. Since, brighter specular reflections correspond to higher glossiness values, in this method we weight preselected pixel by its intensities. The following steps describes the details of the algorithm:
1. BR, TL, BL and TR images processed separately
2. For each such an image: R, G and B channels are flat field corrected by RGB channels of the reference image (Spectralon) if FFC is used
3. Convert RGB image to grayscale.
4. Use multiple thresholds {110, . . . 180, . . . 220} for the corrected B channel and {120} for R and G corrected channels to threshold an image.
5. Multiply each pixel, above the threshold, by its grayscale intensity and sum them up
6. Normalize the result by the number of pixels
7. Resulted weighted number of pixels is obtained by averaging weighted number of pixels calculated for each of BR, TL, BL and TR images.

Number of blobs/Average size of blobs/Largest blobs: Here, we use multiple thresholds to select a number of pixels (to form a blob), where an image is converted to grayscale and 95% of the maximum intensity value is selected. As indicated above, lower thresholds may introduce additional important information especially in case of non-uniform illumination. The main steps of the algorithm are the following:
1. BR, TL, BL and TR images processed separately
2. For each such an image: R, G and B channels are flat field corrected by RGB channels of the reference image (Spectralon), if FFC is used
3. Use multiple thresholds {110, . . . , 180, . . . , 220} for the corrected B channel and {120} for R and G corrected channels to threshold an image.
4. Find connected pixels and approximate it by contours—blobs.
5. Number of blobs: Resulted number of blobs (contours) is obtained by averaging number of contours of BR, TL, BL and TR images.
6. Size of blob: Calculate size of boxes and take the mean/take the largest. Again, the resulted averaged size of blobs/the largest is obtained by averaging the mean contour sizes/the largest of BR, TL, BL and TR images.

The term "plurality" refers to two or more.

The term "substantially" herein, such as in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to". The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention also provides a control system that may control the apparatus or device or system, or that may execute the herein described method or process. Yet further, the invention also provides a computer program product, when running on a computer which is functionally coupled to or comprised by the apparatus or device or system, controls one or more controllable elements of such apparatus or device or system.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention claimed is:

1. A system comprising a sensor for measuring a skin parameter, the sensor comprising (i) a plurality of spatially separated light sources configured to provide light source light, and (ii) a detector configured at a first distance from each of the light sources, wherein the sensor is configured to provide the light source light with optical axes under an angle of incidence selected from the range of 10-80° with the skin at a second distance and to detect reflected light source light, wherein the plurality of spatially separated light sources comprises at least three light sources, wherein the light sources are configured to provide visible light source light, wherein the visible light source light is unpolarized, and wherein the first distance is selected from the range of 10-80 mm, wherein the detector is configured to detect polarized light, wherein the sensor comprises a polarizer configured upstream of the detector, and wherein the polarizer comprises one or more of a segmented polarizer including a pixelated wire grid polarizer with two adjacent pixels having polarization orientations that are perpendicular to each other.

2. The system according to claim 1, wherein the detector comprises a 2D camera, wherein the sensor further comprises a focusing lens configured upstream of the detector, and an aperture configured upstream of the detector and upstream of the focusing lens, wherein the aperture has a diameter selected from the range of 0.1-0.8 mm, and wherein the light sources are configured to provide unpolarized white light source light.

3. The system according to claim 1, wherein the system further comprises an analysis system wherein the analysis system is configured to generate a corresponding skin sensor value in dependence of a sensor signal of the sensor.

4. The system according to claim 3, wherein the system comprises a skin care device, wherein the skin care device comprises the sensor and the analysis system.

5. The system according to claim 3, wherein the system comprises (i) a skin care device, wherein the skin care device comprises the sensor, and (ii) a second device functionally coupled to the skin care device, wherein the second device comprises the analysis system.

6. The system according to claim 1, wherein the pixelated wire grid polarizer includes two or more pixels having different polarization orientations.

7. The system according to claim 1, wherein the sensor is configured to provide the light source light with optical axes under an angle of incidence with the skin at a second distance, wherein the angle of incidence is selected from the range of 50-60°.

8. The system according to claim 1, wherein the sensor is configured to provide the light source light with optical axes under an angle of incidence with the skin at a second distance, wherein the angle of incidence is selected from the range of 52-56°.

9. The system according to claim 1, wherein the device comprises a sensing mode, wherein the light sources are configured to sequentially provide the light source light, wherein the detector is configured to sequentially detect reflected light source light sequentially generated by the light sources, and configured to generate corresponding detector signals, wherein the system further comprises an analysis system, wherein the analysis system is configured to generate a corresponding skin sensor value in dependence of a sensor signal of the sensor, and wherein the skin sensor value is based on an average of respective detector signals.

10. The system according to claim 1, wherein the system further comprises an analysis system wherein the analysis system is configured to generate a corresponding skin sensor value in dependence of a sensor signal of the sensor, wherein the system is configured to create an image of the skin with the detector, wherein the image of the skin comprises a first area wherein a maximum intensity is sensed and a second area at a first image distance from the first area, wherein the first area and second area do not overlap, wherein the system is further configured to generate the skin sensor value based on an intensity dependent of the reflected light source light along a path between the first area and the second area.

11. The system according to claim 1, wherein the sensor has a sensor optical axis, and wherein the fight sources are configured rotationally symmetric around the sensor optical axis.

12. A method of sensing skin gloss, the method comprises providing light source light with the system according to claim 1 to a skin and sensing with the system the reflected light source light reflected at the skin.

13. A data carrier having stored thereon program instructions, which when executed by the system causes the system to execute the method according to claim 12, wherein the system comprises a processor.

14. A sensor for measuring a skin parameter, the sensor comprising:
  a plurality of spatially separated light sources configured to provide source light;
  a detector configured at a first distance from each of the light sources; and
  a polarizer configured upstream of the detector,
  wherein the polarizer comprises one or more of a segmented polarizer including a pixelated wire grid polarizer with two adjacent pixels having polarization orientations that are perpendicular to each other.

15. A system comprising:
  a plurality of spatially separated light sources configured to provide source light to an object for reflection from the object as reflected light;
  a detector configured to detect the reflected light;
  a polarizer configured upstream of the detector; and
  an analyzer configured to generate a sensor value in dependence of a sensor signal of the detector,
  wherein the polarizer comprises one or more of a segmented polarizer including a pixelated wire grid polarizer with two adjacent pixels having polarization orientations that are perpendicular to each other.

16. The system of claim 15, wherein the detector is at a first distance from each of the plurality of spatially separated light sources, wherein the source light is incident on the object at an angle of incidence selected from a range of 10-80°, wherein the object is at a second distance from the detector, the second distance being less than the first distance, wherein the plurality of spatially separated light sources comprises at least three light sources configured to provide visible and unpolarized light as the source light.

17. The system of claim 16, wherein the first distance is selected from the range of 10-80 mm.

* * * * *